United States Patent
Yui et al.

(10) Patent No.: US 6,808,706 B1
(45) Date of Patent: Oct. 26, 2004

(54) METHOD FOR KEEPING THE QUALITY OF AQUEOUS PARENTERAL SOLUTION OF THROMBOMODULIN IN STORAGE AND DISTRIBUTION

(75) Inventors: Masaki Yui, Shizuoka (JP); Akira Yokozawa, Shizuoka (JP); Tomoyo Murata, Shizuoka (JP); Kazuhisa Tsuruta, Shizuoka (JP); Hirotomo Shimizu, Shizuoka (JP)

(73) Assignee: Asaki Kasei Pharma Corporation, Tokyo (JP)

( * ) Notice: Subject to any disclaimer, the term of this patent is extended or adjusted under 35 U.S.C. 154(b) by 0 days.

(21) Appl. No.: 09/509,994

(22) PCT Filed: Oct. 13, 1998

(86) PCT No.: PCT/JP98/04609

§ 371 (c)(1),
(2), (4) Date: May 8, 2000

(87) PCT Pub. No.: WO99/18994

PCT Pub. Date: Apr. 22, 1999

(30) Foreign Application Priority Data

Oct. 15, 1997 (JP) ............................................. 9-281659
Nov. 11, 1997 (JP) ............................................. 9-308523

(51) Int. Cl.$^7$ .......................... C12N 9/00; A61K 38/00; A61K 35/14; A61K 35/16
(52) U.S. Cl. .................... 424/94.3; 435/69.1; 435/69.6; 435/183; 514/2; 514/822; 530/350; 530/380; 930/10
(58) Field of Search ............................... 435/69.1, 69.6, 435/183; 514/2, 822; 530/350, 380; 930/10; 424/94.3

(56) References Cited

U.S. PATENT DOCUMENTS

| | | | |
|---|---|---|---|
| 4,912,207 A | 3/1990 | Majerus et al. | ................ 536/27 |
| 5,202,421 A | * 4/1993 | Kunihiro et al. | ............ 530/350 |
| 5,834,028 A | 11/1998 | Kunihiro et al. | ............ 424/545 |
| 6,034,060 A | 3/2000 | Yamamoto et al. | ........... 514/12 |

FOREIGN PATENT DOCUMENTS

| | | |
|---|---|---|
| JP | 2255699 | 10/1990 |
| JP | 5213998 | 8/1993 |
| JP | 5310787 | 11/1993 |
| JP | 6321805 | 11/1994 |

OTHER PUBLICATIONS

Nursing Procedures, 1993, Springhouse Corp., Charnow et al. eds. pp. 286–287.*

M. Zushi et al., "The Last Three Consecutive Epidermal Growth Factor–like Structures of Human Thrombomodulin Comprise the Minimum Functional Domain for Protein C–activating Cofactor Activity and Anticoagulant Acitivty," Journal of Biological Chemistry, vol. 264, No. 18, pp. 10351–10353, 1989.

K. Nawa et al., "The Glycosaminoglycan of Recombinant Human Soluble Thrombomodulin Affects Antithrombotic Activity in a Rat Model of Tissue Factor–Induced Disseminated Intravascular Coagulation," Thrombosis and Haemostasis, 67(3), pp. 366–370, 1992.

* cited by examiner

*Primary Examiner*—Jon P. Weber
*Assistant Examiner*—Holly Schnizer
(74) *Attorney, Agent, or Firm*—Young & Thompson

(57) ABSTRACT

A method for keeping the quality of an aqueous parenteral solution of thrombomodulin which is not in a frozen or freeze-dried state but in a liquid form in storage and distribution, characterized in that the aqueous thrombomodulin solution containing an effective amount of soluble thrombomodulin and a buffer component exhibiting a buffering activity in a pH range of 5 to 7.0 has a pH of 5 to 7.0 and that (a) the aqueous thrombomodulin solution further contains a surfactant and is in a state aseptically filled into a case or (b) the aqueous thrombomodulin solution is the form of a prefilled syringe preparation produced by aseptically filling the thrombomodulin solution into a syringe substantially without any empty space. This method provides for the storage and distribution of an aqueous parenteral solution of thrombomodulin in a liquid state for a prolonged period and makes it possible to provide an aqueous parenteral solution which is excellent in long-term stability and shaking stability and can save the trouble of dissolving in use.

10 Claims, 1 Drawing Sheet

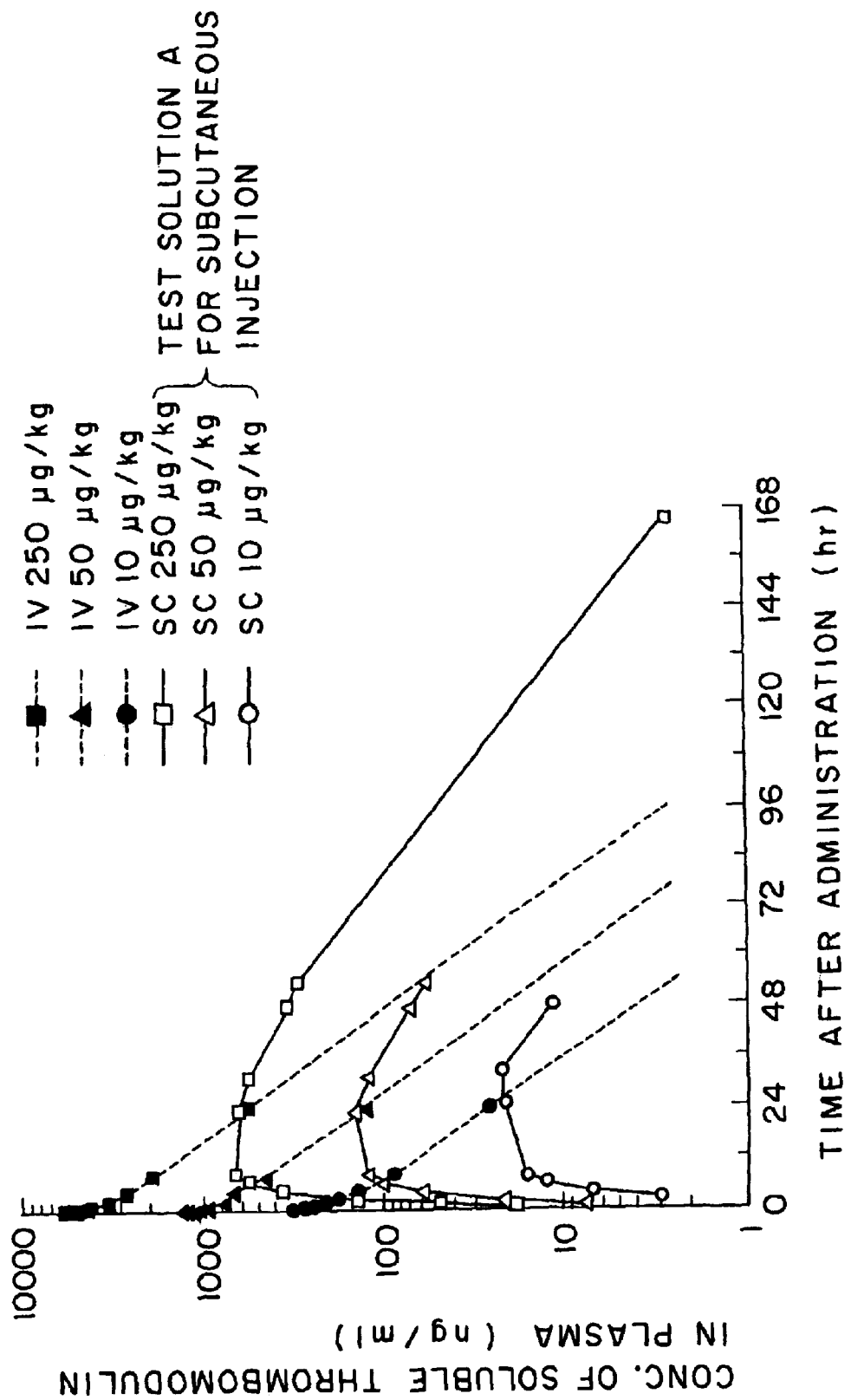

SEQUENCE LISTING

```
<160> NUMBER OF SEQ ID NOS: 6

<210> SEQ ID NO 1
<211> LENGTH: 516
<212> TYPE: PRT
<213> ORGANISM: Homo sapiens
<220> FEATURE:
<223> OTHER INFORMATION: Partial amino acid sequences of a human
      thrombomodulin

<400> SEQUENCE: 1

Met Leu Gly Val Leu Val Leu Gly Ala Leu Ala Leu Ala Gly Leu Gly
 1               5                  10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160
```

-continued

```
Lys Ala Asp Gly Phe Leu Cys Glu Phe His Phe Pro Ala Thr Cys Arg
                165                 170                 175
Pro Leu Ala Val Glu Pro Gly Ala Ala Ala Ala Val Ser Ile Thr
            180                 185                 190
Tyr Gly Thr Pro Phe Ala Ala Arg Gly Ala Asp Phe Gln Ala Leu Pro
            195                 200                 205
Val Gly Ser Ser Ala Ala Val Ala Pro Leu Gly Leu Gln Leu Met Cys
    210                 215                 220
Thr Ala Pro Pro Gly Ala Val Gln Gly His Trp Ala Arg Glu Ala Pro
225                 230                 235                 240
Gly Ala Trp Asp Cys Ser Val Glu Asn Gly Gly Cys Glu His Ala Cys
                245                 250                 255
Asn Ala Ile Pro Gly Ala Pro Arg Cys Gln Cys Pro Ala Gly Ala Ala
                260                 265                 270
Leu Gln Ala Asp Gly Arg Ser Cys Thr Ala Ser Ala Thr Gln Ser Cys
    275                 280                 285
Asn Asp Leu Cys Glu His Phe Cys Val Pro Asn Pro Asp Gln Pro Gly
    290                 295                 300
Ser Tyr Ser Cys Met Cys Glu Thr Gly Tyr Arg Leu Ala Ala Asp Gln
305                 310                 315                 320
His Arg Cys Glu Asp Val Asp Asp Cys Ile Leu Glu Pro Ser Pro Cys
                325                 330                 335
Pro Gln Arg Cys Val Asn Thr Gln Gly Gly Phe Glu Cys His Cys Tyr
                340                 345                 350
Pro Asn Tyr Asp Leu Val Asp Gly Glu Cys Val Glu Pro Val Asp Pro
                355                 360                 365
Cys Phe Arg Ala Asn Cys Glu Tyr Gln Cys Gln Pro Leu Asn Gln Thr
    370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
                405                 410                 415
Cys Asp Pro Asn Thr Gln Ala Ser Cys Glu Cys Pro Glu Gly Tyr Ile
            420                 425                 430
Leu Asp Asp Gly Phe Ile Cys Thr Asp Ile Asp Glu Cys Glu Asn Gly
            435                 440                 445
Gly Phe Cys Ser Gly Val Cys His Asn Leu Pro Gly Thr Phe Glu Cys
    450                 455                 460
Ile Cys Gly Pro Asp Ser Ala Leu Val Arg His Ile Gly Thr Asp Cys
465                 470                 475                 480
Asp Ser Gly Lys Val Asp Gly Gly Asp Ser Gly Ser Gly Glu Pro Pro
                485                 490                 495
Pro Ser Pro Thr Pro Gly Ser Thr Leu Thr Pro Pro Ala Val Gly Leu
            500                 505                 510
Val His Ser Gly
        515

<210> SEQ ID NO 2
<211> LENGTH: 516
<212> TYPE: PRT
<213> ORGANISM: Homo sapiens
<220> FEATURE:
<223> OTHER INFORMATION: Partial amino acid sequences of a human
      thrombomodulin

<400> SEQUENCE: 2
```

```
Met Leu Gly Val Leu Val Leu Gly Ala Leu Ala Leu Ala Gly Leu Gly
 1               5                  10                  15
Phe Pro Ala Pro Ala Glu Pro Gln Pro Gly Gly Ser Gln Cys Val Glu
                 20                  25                  30
His Asp Cys Phe Ala Leu Tyr Pro Gly Pro Ala Thr Phe Leu Asn Ala
             35                  40                  45
Ser Gln Ile Cys Asp Gly Leu Arg Gly His Leu Met Thr Val Arg Ser
         50                  55                  60
Ser Val Ala Ala Asp Val Ile Ser Leu Leu Asn Gly Asp Gly Gly
 65                  70                  75                  80
Val Gly Arg Arg Arg Leu Trp Ile Gly Leu Gln Leu Pro Pro Gly Cys
                 85                  90                  95
Gly Asp Pro Lys Arg Leu Gly Pro Leu Arg Gly Phe Gln Trp Val Thr
                100                 105                 110
Gly Asp Asn Asn Thr Ser Tyr Ser Arg Trp Ala Arg Leu Asp Leu Asn
            115                 120                 125
Gly Ala Pro Leu Cys Gly Pro Leu Cys Val Ala Val Ser Ala Ala Glu
130                 135                 140
Ala Thr Val Pro Ser Glu Pro Ile Trp Glu Glu Gln Cys Glu Val
145                 150                 155                 160
Lys Ala Asp Gly Phe Leu Cys Glu Phe His Phe Pro Ala Thr Cys Arg
                165                 170                 175
Pro Leu Ala Val Glu Pro Gly Ala Ala Ala Ala Val Ser Ile Thr
                180                 185                 190
Tyr Gly Thr Pro Phe Ala Ala Arg Gly Ala Asp Phe Gln Ala Leu Pro
            195                 200                 205
Val Gly Ser Ala Ala Val Ala Pro Leu Gly Leu Gln Leu Met Cys
            210                 215                 220
Thr Ala Pro Pro Gly Ala Val Gln Gly His Trp Ala Arg Glu Ala Pro
225                 230                 235                 240
Gly Ala Trp Asp Cys Ser Val Glu Asn Gly Gly Cys Glu His Ala Cys
                245                 250                 255
Asn Ala Ile Pro Gly Ala Pro Arg Cys Gln Cys Pro Ala Gly Ala Ala
                260                 265                 270
Leu Gln Ala Asp Gly Arg Ser Cys Thr Ala Ser Ala Thr Gln Ser Cys
            275                 280                 285
Asn Asp Leu Cys Glu His Phe Cys Val Pro Asn Pro Asp Gln Pro Gly
            290                 295                 300
Ser Tyr Ser Cys Met Cys Glu Thr Gly Tyr Arg Leu Ala Ala Asp Gln
305                 310                 315                 320
His Arg Cys Glu Asp Val Asp Asp Cys Ile Leu Glu Pro Ser Pro Cys
                325                 330                 335
Pro Gln Arg Cys Val Asn Thr Gln Gly Gly Phe Glu Cys His Cys Tyr
                340                 345                 350
Pro Asn Tyr Asp Leu Val Asp Gly Glu Cys Val Glu Pro Val Asp Pro
            355                 360                 365
Cys Phe Arg Ala Asn Cys Glu Tyr Gln Cys Gln Pro Leu Asn Gln Thr
            370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
                405                 410                 415
```

-continued

```
Cys Asp Pro Asn Thr Gln Ala Ser Cys Glu Cys Pro Glu Gly Tyr Ile
            420                 425                 430
Leu Asp Asp Gly Phe Ile Cys Thr Asp Ile Asp Glu Cys Glu Asn Gly
            435                 440                 445
Gly Phe Cys Ser Gly Val Cys His Asn Leu Pro Gly Thr Phe Glu Cys
        450                 455                 460
Ile Cys Gly Pro Asp Ser Ala Leu Ala Arg His Ile Gly Thr Asp Cys
465                 470                 475                 480
Asp Ser Gly Lys Val Asp Gly Gly Asp Ser Gly Ser Gly Glu Pro Pro
            485                 490                 495
Pro Ser Pro Thr Pro Gly Ser Thr Leu Thr Pro Pro Ala Val Gly Leu
            500                 505                 510
Val His Ser Gly
        515
```

<210> SEQ ID NO 3
<211> LENGTH: 1548
<212> TYPE: DNA
<213> ORGANISM: Homo sapiens
<220> FEATURE:
<223> OTHER INFORMATION: Partial base sequences of a human
      thrombomodulin gene

<400> SEQUENCE: 3

```
atgcttgggg tcctggtcct tggcgcgctg ccctggccg gcctggggtt ccccgcaccc      60
gcagagccgc agccgggtgg cagccagtgc gtcgagcacg actgcttcgc gctctaccccg    120 ggccccgcga ccttcctcaa tgccagtcag atctgcgacg gactgcgggg ccacctaatg    180
acagtgcgct cctcggtggc tgccgatgtc atttccttgc tactgaacgg cgacggcggc    240
gttggccgcc ggcgcctctg gatcggcctg cagctgccac ccggctgcgg cgaccccaag    300
cgcctcgggc cctgcgcgg cttccagtgg gttacgggag acaacaacac cagctatagc    360
aggtgggcac ggctcgacct caatggggct cccctctgcg gcccgttgtg cgtcgctgtc    420
tccgctgctg aggccactgt gcccagcgag ccgatctggg aggagcagca gtgcgaagtg    480
aaggccgatg gcttcctctg cgagttccac ttcccagcca cctgcaggcc actggctgtg    540
gagcccggcg ccgcggctgc cgccgtctcg atcacctacg gcaccccgtt cgcggcccgc    600
ggagcggact tccaggcgct gccggtgggc agctccgccg cggtggctcc cctcggctta    660
cagctaatgt gcaccgcgcc gcccggagcg gtccagggggc actgggccag ggaggcgccg    720
ggcgcttggg actgcagcgt ggagaacggc ggctgcgagc acgcgtgcaa tgcgatccct    780
ggggctcccc gctgccagtg cccagccggc gccgccctgc aggcagacgg gcgctcctgc    840
accgcatccg cgacgcagtc ctgcaacgac ctctgcgagc acttctgcgt tcccaaccccc    900 gaccagccgg gctcctactc gtgcatgtgc gagaccggct accggctggc ggccgaccaa    960
caccggtgcg aggacgtgga tgactgcata ctggagccca gtccgtgtcc gcagcgctgt   1020
gtcaacacac agggtggctt cgagtgccac tgctaccccta actacgacct ggtggacggc   1080
gagtgtgtgg agcccgtgga cccgtgcttc agagccaact gcgagtacca gtgccagccc   1140
ctgaaccaaa ctagctacct ctgcgtctgc gccgagggct cgcgcccat tccccacgag   1200 ccgcacaggt gccagatgtt ttgcaaccag actgcctgtc cagccgactg cgaccccaac   1260
acccaggcta gctgtgagtg ccctgaaggc tacatcctgg acgacggttt catctgcacg   1320
gacatcgacg agtgcgaaaa cggcggcttc tgctccgggg tgtgccacaa cctccccggt   1380
accttcgagt gcatctgcgg gcccgactcg gcccttgtcc gccacattgg caccgactgt   1440
```

```
gactccggca aggtggacgg tggcgacagc ggctctggcg agccccgcc cagcccgacg    1500 cccggctcca ccttgactcc tccggccgtg gggctcgtgc attcgggc                1548
```

<210> SEQ ID NO 4
<211> LENGTH: 1548
<212> TYPE: DNA
<213> ORGANISM: Homo sapiens
<220> FEATURE:
<223> OTHER INFORMATION: Partial base sequences of a human
      thrombomodulin gene

<400> SEQUENCE: 4

```
atgcttgggg tcctggtcct tggcgcgctg gccctggccg gcctggggtt ccccgcaccc     60
gcagagccgc agccgggtgg cagccagtgc gtcgagcacg actgcttcgc gctctacccg    120
ggccccgcga ccttcctcaa tgccagtcag atctgcgacg gactgcgggg ccacctaatg    180
acagtgcgct cctcggtggc tgccgatgtc atttccttgc tactgaacgg cgacggcggc    240
gttggccgcc ggcgcctctg gatcggcctg cagctgccac ccggctgcgg cgaccccaag    300
cgcctcgggc ccctgcgcgg cttccagtgg gttacgggag acaacaacac cagctatagc    360
aggtgggcac ggctcgacct caatggggct cccctctgcg gcccgttgtg cgtcgctgtc    420
tccgctgctg aggccactgt gcccagcgag ccgatctggg aggagcagca gtgcgaagtg    480
aaggccgatg gcttcctctg cgagttccac ttcccagcca cctgcaggcc actggctgtg    540
gagcccggcg ccgcggctgc cgccgtctcg atcacctacg caccccgtt cgcggcccgc    600 ggagcggact ccaggcgct gccggtgggc agctccgccg cggtggctcc cctcggctta    660
cagctaatgt gcaccgcgcc gcccggagcg gtccaggggc actgggccag ggaggcgccg    720
ggcgcttggg actgcagcgt ggagaacggc ggctgcgagc acgcgtgcaa tgcgatccct    780
ggggctcccc gctgccagtg cccagccggc gccgccctgc aggcagacgg gcgctcctgc    840
accgcatccg cgacgcagtc ctgcaacgac ctctgcgagc acttctgcgt tcccaacccc    900
gaccagccgg gctcctactc gtgcatgtgc gagaccggct accggctggc ggccgaccaa    960
caccggtgcg aggacgtgga tgactgcata ctggagccca gtccgtgtcc gcagcgctgt    1020
gtcaacacac aggtggctt cgagtgccac tgctacccta actacgacct ggtggacggc    1080
gagtgtgtgg agccccgtgga cccgtgcttc agagccaact gcgagtacca gtgccagccc    1140
ctgaaccaaa ctagctacct ctgcgtctgc gccgagggct tcgcgcccat tcccacgag    1200 ccgcacaggt gccagatgtt ttgcaaccag actgcctgtc cagccgactg cgaccccaac    1260
acccaggcta gctgtgagtg ccctgaaggc tacatcctgg acgacggtt catctgcacg    1320 gacatcgacg agtgcgaaaa cggcggcttc tgctccgggg tgtgccacaa cctcccggt    1380 accttcgagt gcatctgcgg gcccgactcg gcccttgccc gccacattgg caccgactgt    1440
gactccggca aggtggacgg tggcgacagc ggctctggcg agccccgcc cagcccgacg    1500 cccggctcca ccttgactcc tccggccgtg gggctcgtgc attcgggc                 1548
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      peptide
<223> OTHER INFORMATION: Synthetic DNA for mutation

<400> SEQUENCE: 5

```
aatgtggcgg gcaagggccg a                                          21

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      substrate

<400> SEQUENCE: 6

Leu Ser Thr Arg
 1
```

METHOD FOR KEEPING THE QUALITY OF AQUEOUS PARENTERAL SOLUTION OF THROMBOMODULIN IN STORAGE AND DISTRIBUTION

This application is a 371 of PCT JP 98/04609.

INDUSTRIAL FIELD OF APPLICATION

The present invention relates to a method for maintaining the quality of aqueous injection preparation of thrombomodulin in a non-frozen or non-freeze-dried liquid form over its storage/transportation and to an aqueous injection preparation of thrombomodulin stable over its storage/transportation.

PRIOR ART

Thrombomodulin (in the following, abbreviated sometimes as TM) is a substance having a function of coupling specifically with thrombin and accelerating the activation of protein C by thrombin remarkably. Protein C consists of a vitamin K dependent protein which plays an important role in the coagulation fibrinolysis system and is activated by the action of thrombin into activated protein C. It has been known that activated protein C will inactivate the activated coagulation factors V and VIII in the blood coagulation system of living body and that it participates in the production of plasminogen activator which reveals a thrombolytic function (See Koji Suzuki, "Igaku-no Ayumi (Progress in Medical Science)", Vol. 125, 901 (1983))

Thus, it has been recognized that thrombomodulin accelerates activation of protein C by thrombin to produce a large amount of activated protein C exhibiting inhibitive action to blood coagulation and thrombolytic function and is useful as an anticoaglant and as a thrombolytic agent. It has heretofore been expected to use thrombomodulin for therapy and prophylaxis of, such as acute coronary syndrome (ACS), for example, myocardiac infarction and unstable angina, for reconstruction of coronary circulation; for therapies and prophylaxes of thromboses, such as acute and chronic cerebral thromboses and acute and chronic arterial and venous peripheral thromboses; peripheral blood vessel obstruction, such as Buerger disease and Raynaud disease; obstructive arteriosclerosis; blood vessel inflammation, such as systemic lumpus erythematodes (SLE), Becet disease and Kawasaki disease; and for therapies and prophylaxes of functional disorders pursuant to a cardiac surgery, complications pusuant to an organ transplantation, disease of intravascular coagulation (DIC), angina pectoris, transient cerebral ischemic attack, gestational toxicosis, diabetes, liver venoocclusive diseases (VOD), such as venoocclusive diseases following fulminant hepatitis or after bone marrow transplantation, and deep venous thrombosis (DVT).

In the past, thrombomodulin was confirmed and isolated as a glycoprotein appearing on the endothelial cells of blood vessel of animals, including human. Our group of inventors of the present invention had succeeded to clone it for the first time. Thus, the inventors had performed cloning of genes of a precursor of a human thrombomodulin having a signal peptide from the human lung cDNA library using a technique of genetic engineering, whereby the entire gene sequence of the thrombomodulin was analyzed and its amino acid sequence having 575 residues including a signal peptide of 18 amino acid residues was made clear (See Japanese Patent Kokai Sho 64-6219 A). It has been known that a mature thrombomodulin with the signal peptide being cut is composed of five domains, namely, the $NH_2$-terminal domain (1st to 226th amino acid residue, in the order from the $NH_2$-terminus), the domain having 6 EGF-like structures (227th to 462nd residue), the O-glycosylation site-rich domain (463rd to 498th residue), the transmembrane domain (499th to 521st residue) and the cytoplasmic domain, enumerated respectively in the sequential order from the $NH_2$-terminus, wherein the segment exhibiting the activity corresponding to that of the full length thrombomodulin, namely, the least active unit thereof, is constituted of the segemnt consisting of the fourth, fifth and sixth EGF-like structures in the domain having 6 EGF-like structures as enumerated in the order from the $NH_2$-terminus (See M. Zushi et al, J. Biol. Chem., 246, 10351–10353 (1989)).

It has been confirmed that at least such a thrombomodulin which is prepared so as to eliminate the transmembrane domain has a nature of being clearly dissolved in water even without using any surfactant (in the following, referred to sometimes as "soluble thrombomodulin") and, for example, a thrombomodulin composed of only the three domains, i.e. the $NH_2$-terminal domain, the domain having 6 EGF-like structures and the O-glycosylation site-rich domain, namely, composed of the amino acid sequence from the 19th to 516th amino acid residues of the sequence listing SEQ ID NO:1, can be obtained by applying a gene recombination technology and that the so-obtained recombinant thrombomodulin has an activity which is the same as that of natural thrombomodulin (Japanese Patent Kokai Sho 64-6219 A).

By the way, as recognized in many cases, genes may suffer from natural and artificial mutations due to inspection work upon, for example, their isolation etc., without exception for human in which also a polymorphic mutation had been discovered, wherein two mutants of the precursor of human thrombomodulin constituted of the amino acid sequence composed of the above-mentioned 575 amino acid residues were confirmed, in which the amino acid residue at the 473rd site consists of Val, for the one, and in which this amino acid residue consists of Ala, for the other. This corresponds, in the base sequence coding such amino acids, to mutations of T and C of the 1418th site, respectively (Wen et al, Biochemistry, 26, 4350–4357 (1987)). They do reveal, however, no difference in the activity and in the physical properties from each other and can be regarded as being substantially identical. Therefore, the above-mentioned human thrombomodulin constituted of the amino acid sequence of the sequence listing SEQ ID NO:1 is regarded as one of polymorphs of the peptide of thrombomodulin composed of the amino acid sequence of sequence listing SEQ ID NO: 2 and both should be judged as substantially identical with each other.

On the other hand, thrombomodulin preparations have currently been distributed steadily for practical use in a form of freeze-dried medicinal pharmaceutical. Meanwhile, it had been discovered that, in the process of freeze-drying of a thrombomodulin-containing aqueous solution, a part of thrombomodulin is converted, though in a minute amount, into a polymeric matter due to a denaturization to form a polymer in which several molecules of thrombomodulin are held in association. For resolving this problem, the inventors made sound researches, whereby they reached the discovery that denaturization of thrombomodulin upon freeze-drying thereof could be prevented, of which invention was previously applied for a patent (Japanese Patent Kokai Hei 6-321805 A).

THEME TO BE SOLVED BY THE INVENTION

Despite of the above circumstances, requests had been raised for providing a novel preparation in a non-frozen or non-freeze-dried form which can be used simply and easily and can be produced at a lower production cost.

MEANS FOR SOLVING THE THEME

The inventors of the present invention had investigated the possibility of realizing an aqueous injection preparation of thrombomodulin which can afford to avoid incorporation of freeze-drying process and to eliminate necessity of dissolution procedure upon practical use, under an attempt of developing a new preparation other than the freeze-dried preparation. While it is requested at first for an aqueous injection preparation that its residual potency after storage over a long period of time at 5° C. to room temperature should not be decreased to a considerable extent (i.e. a long term stability), investigations have shown that it is not easy to attain such a long term stability. To our surprise, it was further found that an aqueous injection preparation may in some cases become turbid by shaking it. It is expected enough that a liquid preparation maybe subjected to a shaking motion, though at different intensity levels, on its distribution, such as transportation. Such a problem is not encountered for conventional freeze-dried powdery preparation. Thus, a new and unexpected problem was recognized by us for a stability against shaking of aqueous injection preparation. Presence of any insoluble matter in an injection preparation may cause occasionally a fatal accident in patients, in particular, having disorders in the circulatory organs and, thus, the problem in the stability against shaking for obviating occurence of turbidity upon shaking of aqueous injection preparation mentioned above is a very significant obstruction to be overcome.

In summary, it has heretofore been difficult to prepare an aqueous injection preparation which can permit to store/transport in a liquid form as such over a long period of time, since any injection preparation which is satisfactory with respect to the long term stability and to the stability against shaking can never be obtained by simply dissolving thrombomodulin in water, in despite of the circumstances that an aqueous injection preparation has advantageous features that it can conveniently be administered to patient without necessitating any procedure of dissolving in the water for injection upon practical use and that it can be produced economically and more easily due to elimination of the procedure of freeze-drying, as compared with the conventional freeze-dried preparation.

The inventors had conducted sound researches for obviating the above described problems and found that all these problems were able to be solved by keeping a certain condition, which has led to the completion of the present invention.

Thus, the present invention provides for a method for maintaining the quality of aqueous injection preparation of thrombomodulin in a non-frozen or non-freeze-dried liquid form over its storage and transportation, characterized in that the aqueous injection preparation of thrombomodulin is prepared as an aqueous solution having a pH value in the range from 5 to 7.0 and containing (a) soluble thrombomodulin in an effective amount and a buffer component revealing a buffering action in a pH rang between 5 and 7.0, wherein the aqueous solution of thrombomodulin has either the following characteristic feature a) or b), namely,
a) that it contains further a surfactant and is filled aseptically in a container or
b) that it consists of a prefilled syringe preparation filled aseptically in a syringe container so as to exclude any substantial gas space therein.

Therefore, the first embodiment form of the method for maintaing the quality of aqueous injection preparation according to the present invention consists in that the aqueous injection preparation of thrombomodulin, which is characterised in that it is prepared as an aqueous solution having a pH value in the range from 5 to 7.0 and containing a soluble thrombomodulin in an effective amount, a buffer component revealing a buffering action in a pH range between 5 and 7.0 and a surfactant and is filled in a container aseptically, is stored/transported in a liquid form over a long period of time.

The second embodiment form of the method for maintaing the quality of aqueous injection preparation according to the present invention consists in that the aqueous injection preparation of thrombomodulin, which is characterised in that it is prepared as an aqueous solution having a pH value in the range from 5 to 7.0 and containing a soluble thrombomodulin in an effective amount and a buffer component revealing a buffering action in a pH range between 5 and 7.0 and consists of a prefilled syringe preparation filled aseptically in a syringe container so as to exclude any substantial gas space therein, is stored/transported in a liquid form over a long period of time.

The third favorable embodiment form of the method for maintaing the quality of aqueous injection preparation according to the present invention consists in that the aqueous injection preparation of thrombomodulin, which is characterised in that it is prepared as an aqueous solution having a pH value in the range from 5 to 7.0 and containing a soluble thrombomodulin in an effective amount, a buffer component revealing a buffering action in a pH range between 5 and 7.0 and a surfactant and consists of a prefilled syringe preparation filled aseptically in a syringe container so as to exclude any substantial gas space therein, is stored/transported in a liquid form over a long period of time.

The present invention also provides for a method for realizing a long term stability and a stability against shaking of an aqueous injection preparation of thrombomodulin in a non-frozen or non-freeze-dried liquid form, characterized in that the aqueous injection preparation of thrombomodulin is prepared as an aqueous solution having a pH value in the range from 5 to 7.0 and containing a soluble thrombomodulin in an effective amount and a buffer component revealing a buffering action in a pH range between 5 and 7.0, wherein the aqueous solution of thrombomodulin has either the following characteristic feature a) or b), namely,
a) that it contains further a surfactant and is filled aseptically in a container or
b) that it consists of a prefilled syringe preparation filled aseptically in a syringe vessel so as to exclude any substantial residual gas space therein.

The aqueous injection preparation of thrombomodulin to be used in the method according to the present invention in a non-frozen or non-freeze-dried liquid form, prepared as an aqueous solution having a pH value in the range from 5 to 7.0 and containing a soluble thrombomodulin in an effective amount and a buffer component revealing a buffering action in a pH range between 5 and 7.0, is superior in the stability for long term storage and in the stability against shaking and suitable for storing/transporting over a long period of time and is characterized in that the aqueous solution of thrombomodulin has a pH value in the range from 5 to 7.0 and has either the following characteristic feature a) or b), namely,
a) that it contains further a surfactant and is filled aseptically in a container or
b) that it consists of a prefilled syringe preparation filled aseptically in a syringe vessel so as to exclude any substantial residual gas space therein.

Thus, the first aspect of the aqueous injection preparation of thrombomodulin according to the present invention consists in an aqueous injection preparation of thrombomodulin in a non-frozen or non-freeze-dried liquid form, superior in the stability for long term storage and in the stability against shaking and suitable for storing/transporting over a long period of time, characterized in that the aqueous injection preparation of thrombomodulin has a pH value in the range from 5 to 7.0, contains a soluble thrombomodulin in an effective amount, a buffer component revealing a buffering action in a pH range between 5 and 7.0 and a surfactant and is filled in a container aseptically.

The second aspect of the aqueous injection preparation of thrombomodulin according to the present invention consists in an aqueous injection preparation of thrombomodulin in a non-frozen or non-freeze-dried liquid form, superior in the stability for long term storage and in the stability against shaking and suitable for storing/transporting over a long period of time, characterized in that the aqueous injection preparation of thrombomodulin is a prefilled syringe preparation which has a pH value in the range from 5 to 7.0, contains a soluble thrombomodulin in an effective amount and a buffer component revealing a buffering action in a pH range between 5 and 7.0 and which is filled in a syringe container aseptically so as to exclude any substantial gas space therein.

The third aspect of the aqueous injection preparation of thrombomodulin according to the present invention consists in an aqueous injection preparation of thrombomodulin in a non-frozen or non-freeze-dried liquid form, superior in the stability for long term storage and in the stability against shaking and suitable for storing/transporting over a long period of time, characterized in that the aqueous injection preparation of thrombomodulin is a prefilled syringe preparation which has a pH value in the range from 5 to 7.0, contains a soluble thrombomodulin in an effective amount, a buffer component revealing a buffering action in a pH range between 5 and 7.0 and a surfactant and which is filled in a syringe container aseptically so as to exclude any substantial gas space therein.

The term "thrombomodulin" as used in the specification of this patent application refers, without any special restriction, to every substance having a function of being bound to thrombin to bring about acceleration of the activation of protein C by the thrombin. In the context of this specification, the term "soluble thrombomodulin" refers to a substance which exhibits an activity as the above-mentioned "thrombomodulin" and is soluble in water easily even in the absence of surfactant and which may favorably exhibit a solubility of, for example, at least 1 mg/ml, preferably at least 3 mg/ml, especially preferably at least 6 mg/ml, in the water for injection. As favorable examples of the soluble thrombomodulin, peptides having a molecular weight, as determined by SDS-polyacryamide gel electrophoresis in non-reduced state, of 66,000±10,000, exhibiting a function for accelerating the activation of protein C by thrombin and soluble in the water for injection at least at a concentration of 6 mg/ml may be enumerated. As other favorable soluble thrombomodulins, those peptides which are constituted of amino acid sequences including the amino acid sequence composed of the amino acid residues from the 19th site to the 29th site in the sequence listing SEQ ID NO: 1, exhibiting a function for accelerating the activation of protein C by thrombin and soluble in water are exemplified. Further examples of favorable soluble thrombomodulins include those consisting of the following i) and ii), namely, i) thrombomodulins which are constituted of an amino acid sequence composed of the 19th site to the 516th site amino acid residues in the sequence listing SEQ ID NO: 1 and ii) thrombomodulins which comprise an amino acid sequence composed of those amino acids in which one or more amino acid residues in the amino acid sequence given above are replaced or removed or one or more amino acid residues are added thereto, and exhibiting a function for accelerating the activation of protein C by thrombin.

As the soluble thrombomodulin, there may further be enumerated peptides constituted of amino acid sequences including at least the 4th, 5th and 6th structures, as enumeratd in the sequential order from the $NH_2$-terminus, which are regarded as constituting the smallest active unit of thrombomodulin, in the domain having 6 EGF-like structures (for example, those of Nos. 367 to 480 sites in the sequence listing SEQ ID NO: 1 and the sequence listing SEQ ID NO: 2 for human thrombomodulin). Especially preferred soluble thrombomodulins among them are those peptides which can be produced by transformed cells obtained by transfecting the DNA segment coding the amino acid sequence of the sequence listing SEQ ID NO: 1 or of the sequence listing SEQ ID NO: 2 to a host cell using a vector. As one preferred example of the peptides obtainable from the transformed cells, namely, soluble thrombomodulins, there may be enumerated the peptides constituted of the amino acid sequences composed of the Nos. 19 to 516 sites of the sequence listing SEQ ID NO: 1 and of the sequence listing SEQ ID NO: 2. Others may include, in accordance with each specific host cell, those in which the signal peptide remains as such and which are constituted of the amino acid sequences from the No. 17 to the No. 516 site of the sequence listing SEQ ID NO: 1 and of the sequence listing SEQ ID NO: 2 and mixtures of them. Of course these peptides have quite high solubilities in water which is sufficient for satisfying the prescribed solubility explained above. It is enough for these peptides only that they have the above-mentioned amino acid sequence and no restriction is made therefor, wherein it is no matter whether they have glycosyl chains or not. It is even possible to utilize soluble peptides which are obtainable from human urine and the like. While the kind, the site of addition and the degree of addition of the glycosyl chain in the peptide may be different in accordance with each specific host cell, use of such peptide is not restricted thereby. The peptides composed of the amino acid residues from the No. 367 site to the No. 480 site of the sequence listing SEQ ID NO: 1 and of the sequence listing SEQ ID NO: 2 themselves have a high stability against shaking and may, in any case, result in a favorable aqueous preparation, nevertheless, it is to be understood that it is necessary to increase the stability against shaking by having resort to the technique according to the present invention, for the soluble thrombomodulins having the above-mentioned molecular weight, namely, 66,000± 10,000 in non-reduced state, for example, the soluble thrombomodulin constituted of the amino acid sequence of the residues from No. 19 site to No. 516 site of the sequence listing SEQ ID NO: 1, the soluble thrombomodulin constituted of the amino acid sequence of the residues from No. 19 site to No. 516 site of the sequence listing SEQ ID NO: 2, the soluble thrombomodulin obtained by transfecting a DNA segment coding the amino acid sequence described in the sequence listing SEQ ID NO: 1 to a host cell and the soluble thrombomodulin obtained by transfecting a DNA segment coding the amino acid sequence described in the sequence listing SEQ ID NO: 2 to a host cell.

For the host cell, there may be enumerated cells of, for example, Chinese hamster ovary (CHO), COS-1, COS-7, VERO (ATCC CCL-81), BHK, canin-originated MDCK and hamster AV-12-664, as well as human-originated cells of, such as HeLa, WI38 and human 293. As the CHO cell, DHFR⁻ CHO cell is more preferred. In the course of gene manipulation, various microorganisms, such as *Escherichia coli* and the like, are employed frequently, wherein it is favorable to choose a host-vector system adapted for each purpose and, thus, an adequate vector system should also be selected for each of the above host cells.

The gene of each thrombomodulin to be incorporated in the genetic recombination technique has been cloned and production examples using the genetic recombination technique for thrombomodulin have been disclosed, in addition to the technique of purification for obtaining a purified product (See Japanese Patent Kokais Sho 64-6219 A, Hei 2-255699 A, Hei 5-213998 A, Hei 5-310787 A and Hei 7-155176 A as well as J. Biol. Chem., 264, 10351–10353 (1989)). Therefore, the thrombomodulin to be used according to the present invention can be produced using the techniques described in the above-cited literatures or by means of a technique corresponding to them. For example, there is disclosed in Japanese Patent Kokai Sho 64-6219 A *Escherichia coli* K-12 strain DH5 (with ATCC Deposition No. 67283) having the plasmid psV2TMJ2 containing the DNA coding the entire length of a thrombomodulin, while the applicant of the present invention made again a deposition of the same strain (*Escherichia coli* DH5/psV2TMJ2) at the Institute of Life Engineering of Agency of Industrial Science and Technology of the Ministry of International Trade and Industry at No. 1-3, Higashi 1 Chome, Tsukuba City, Ibaragi Prefecture, Japan, on Jun. 19th, 1996. The Receipt No. was FERM BP-5570. Using, as the starting material, this DNA which codes the entire length of thrombomodulin, the soluble thrombomodulin to be used according to the present invention can be obtained by a known gene manipulation technique.

While the soluble thrombomodulin to be used according to the present invention may be produced by a known technique or a technique corresponding thereto, it is possible therefor to refer to the literatures of, for example, Yamamoto et al (Japanese Patent Kokai Sho 64-6219 A, Cf. Examples) and Japanese Patent Kokai Hei 5-213998 A, given above. Thus, it is possible to obtain the DNA coding the amino acid sequence of the sequence listing SEQ ID NO: 1, by processing the gene of a human thrombomodulin by a gene manipulation technique and, if necessary, to modify it. Such a modification may include a site-specific mutation of the codon that codes the amino acid at the 473th site of the sequence listing SEQ ID NO: 1 (especially the base at the 1418th site) for obtaining the DNA which codes the amino acid sequence of the sequence listing SEQ ID NO: 2, in accordance with the method described in Method in Enzymology, 100, 468 (1983), Academic Press. For example, using a DNA fragment containing the base sequence of the sequence listing SEQ ID NO: 3 and a synthetic DNA for mutation containing the base sequence shown in the sequence listing SEQ ID NO: 5, the above-mentioned site-specific mutation is performed to obtain the DNA which codes the amino acid sequence of the sequence listing SEQ ID NO: 2. The so-obtained DNA can then be integrated into, for example, Chinese hamster ovarian cells to obtain corresponding transformed cells, among which cells chosen pertinently are cultured and, from the culture mixture thereof, the soluble thrombomodulin purified by a known technique is obtained. It is favorable, as mentioned previously, that the DNA which codes the amino acid sequence of the sequence listing SEQ ID NO: 1 is trans- fected to the host cell. The technique for producing the soluble thrombomodulin to be used according to the present invention should not be restricted only to the above-described procedures but many alternatives may be possible including, for example, by recourse to a technique in which the thrombomodulin or soluble thrombomodulin is extracted from a tissue, from a tissue culture mixture, from human urine or so on, with subsequent purification and, if necessary, with further treatment by a proteolytic enzyme.

The isolation and purification of the soluble thrombomodulin from the supernatant or from the culture mixture from the above technique can be performed in a known technique (See, for example, "Fundamental Experimental Methods with Proteins, Enzymes", edited by Buichi Horlo). Use of ion-exchange chromatography based on the interaction between the thrombomodulin and a chromatography stationary phase carrier on which a functional group with ionic charge reverse to that of the thrombomodulin is fixed is also preferable. Also an affinity chromatography based on the specific affinity to the thrombomodulin may favorably be exemplified. As a favorable example of adsorbent to be used, there may be enumerated antibodies of thrombomodulin and of thrombin, which may constitute a ligand of the thrombomodulin. For these antibodies, those of thrombomodulin capable of recognizing an adequate function or an adequate epitope can be utilized, examples of which include those disclosed in, for example, Japanese Patent Publication Hei 5-42920 B and Japanese Patent Kokais Sho 64-45398 A and Hei 6-205692 A. Further, a gel filtration chromatography and an ultrafiltration technique realized with respect to the molecular size of the thrombomodulin. Furthermore, there may be employed a hydrophobic chromatography based on a hydrophobic interaction between the carrier of the stationary phase on which a hydrophobic group is bound and the hydrophobic site of the thrombomodulin. The above-mentioned techniques may be employed in an adequate combination. The degree of purification of the soluble thrombomodulin may adequately be selected in accordance with each specific application, while it is favorable to purify it up to such a degree that a single band will be obtained by, for example, electro-phoresis, preferably, SDS-PAGE, or a single peak will be obtained by, for example, gel permeation HPLC or reversed phase HPLC.

Concretely exemplifying the procedures of purification, a technique in which the purification is proceeded taking a thrombomodulin activity into account as a parameter may be employed, wherein, for example, the supernatant or the culture mixture is treated by Q-Sepharose-FF of an ion-exchange column to collect fractions exhibiting an activity of thrombomodulin, which are then subjected to the proper purification by diisopropylphosphoryl thrombin agarose (DIP-TB), followed by collection of fractions exhibiting higher activity of thrombomodulin, which are then subjected to gel permeation chromatography to realize collection of thrombomodulin-active fractions, in order to obtain a pure soluble thrombomodulin product (See Gomi et al, Blood, 75, 1396–1399 (1990)). As the parameter for the activity of thrombomodulin, there may be utilize, for example, the activity of thrombomodulin to accelerate the activation of protein C. As another purification technique, the following method may also be exemplified:

The thrombomodulin is subjected to an ion-exchange chromatography using an adequately selected ion-exchange resin exhibiting a better adsorbing performance for the thrombomodulin. An especially preferred method utilizes Q-Sepharose-FF equlibrated with 0.02 M Tris-HCl buffer solution (pH=7.4) containing 0.18 M NaCl. The retained thrombomodulin can be eluted out after being washed adequately, using, for example, 0.02 M Tris-HCl buffer solution (pH=7.4) containing 0.3 M NaCl, to obtain a crude product of thrombomodulin.

Thereafter, this product may be subjected to a purification step by, for example, an affinity chromatography using a resin on which a substance having a specific affinity to thrombomodulin is bound. As preferable examples, a DIP-thrombin-agarose column and a column with an anti-thrombomodulin monoclonal antibody may be enumerated. The DIP-thrombin-agarose column can be preliminarily treated by being equilibrated with, for example, a 20 mM Tris-HCl buffer solution (pH=7.4) containing 100 mM NaCl and 0.5 mM calcium chloride, whereupon the column is charged with the above-mentioned crude product, followed by an adequate washing with subsequent elution with, for example, a 0.20 mM Tris-HCl buffer solution (pH=7.4) containing 1.0 M NaCl and 0.5 mM calcium chloride, to obtain a purified product of the soluble thrombomodulin. In the case of the anti-thrombomodulin monoclonal antibody column, the column is filled with Sepharose 4B (of the firm Pharmacia) which has been treated in such a manner that the Sepharose particles in a state activated preliminarily by CNBr are brought into contact with a 0.1 M NaHCO, buffer solution (pH=8.3) containing 0.5 M NaCl and an anti-thrombomodulin monoclonal antibody dissolved therein so as to cause the anti-thrombomodulin monoclonal antibody to be bound onto the Sepharose particles. Then, the column is equilibrated beforehand with, for example, a 20 mM phosphate buffer solution (pH=7.3) containing 1.0 M NaCl, followed by washing adequately, before the retained thrombomodulin is eluted out with, for example, a 100 mM glycine-HCl buffer solution (pH=3.0) containing 0.3 M NaCl.

The so-obtained solution of the purified soluble thrombomodulin is then charged in a column filled with a cation-exchange resin, preferably a strongly acidic cation-exchange resin, such as SP-Sepharose FF (of the firm Pharmacia), which has been equilibrated in general in a condition of, for example, a specific conductivity of 25–34 ms/cm and a pH value of 3–4, though variable in accordance with the salt concentration, determination accuracy of pH and the species of the molecule. The above-mentioned specific conductivity value may more preferably be in the range of 30±3 ms/cm and the pH value may preferably be in the range of 3.0–3.7, more preferably be 3.5±0.1. While it is preferable to use a buffer solution containing dissolved therein a salt at a suitable concentration, wherein, among various possible conditions, a buffure solution of, for example, a 50–150 mM having a pH of 3–4 containing 0.25–0.32 M, preferably 0.3±0.1 M NaCl may be enumerated. While there is no restriction as to the kind of the buffer solution, they may be selected among, for example, glycine-HCl, citric acid-disodium citrate, sodium citrate and acetic acid. More concretely, a 100 mM glycine-HCl buffer solution (pH=3.5) containing 300 mM NaCl may be exemplified. The specific conductivity can be determined easily using a portable conductivity meter (Model P-series CM-11P, an apparatus of To a Electronics Ltd., with standard conversion temperature of 25° C.).

The column prepared as above is then started to pass therethrough with, for example, a 100 mM glycine-HCl buffer solution (pH=3.5, specific conductivity=31 ms/cm) containing 300 mM NaCl, whereupon an eluent fraction is obtained by collecting the passed-by eluent from the start of rising up of the 280 nm absorbance peak from the absorbance for the mere passed-by blank fraction to the end of dropping down thereof, which is then neutralized with an adequate buffer solution, whereby a high purity product of soluble TM purified up to such a degree that it has substantially no content of the substances originated from serum and from antibody can be obtained. As described afterwards, it has been confirmed that removal of the substances originated from serum and antibody can efficiently be removed with better reproducibility by using this column. Of course, they can be concentrated adequately by means of an ultrafiltration.

Further, it is also preferable to carry out exchange of the buffer solution by means of gel filtration. For example, a column of Sephacryl S-300 or S-200 which has been equilibriated with a 20 mM phosphate buffer solution (pH=7.3) containing 50 mM NaCl is loaded with a high purity product concentrated by an ultrafiltration and the column is subjected to a developing fractionation with a 20 mM phosphate buffer solution (pH=7.3) containing 50 mM NaCl, followed by collecting the fractions which show an activity for acceleration of protein C activation by thrombin when examined for such activity and performing exchange of the buffer solution, whereby a high purity product can be obtained.

In many purification processes, the aqueous injection preparation to be used according to the present invention should be obtained without necessitating any special procedure of, such as, addition and adjustment, when a solution containing the buffer component(s) and surfactant(s) permitting to reach finally the condition of pH etc. corresponding to those prescribed according to the present invention can be employed. In general, however, a practice of addition of necessary components etc. to the resulting soluble thrombomodulin solution is simple and convenient and is preferred.

For the buffer component(s) to be employed according to the present invention, there is no special restriction and any one which permits adjustment of pH at a value in the range from 5 to 7.0 and which reveals a buffering action within this range may be employed. Further, a preferred range of pH resides in 5.5–6.5. For example, one or more kinds selected from the group consisting of phosphoric acid, carboxylic acids and/or the water-soluble salts of them may be employed each in an effective amount. As the carboxylic acids and/or water-soluble salts thereof, there may be enumerated, for example, one or more selected from the group consisting of acetic acid, propionic acid, butyric acid, valeric acid, malonic acid, succinic acid, glutaric acid, tartaric acid, fumaric acid, malic acid and/or water-soluble salts of them, wherein special preference is given to phosphoric acid, acetic acid and/or water-soluble salts of them. There is no special restriction as to the water-soluble salts, so long as permitted pharmaceutically, and they include, for example, sodium and potassium salts.

For the container to be employed according to the the present invention, there is no special restriction so long as the material of the container and the configuration thereof are adapted for aseptic filling. There may be exemplified glass syringe (provided with a rubber cap and rubber stopper for premitting asceptic filling), glass vial (with stopper) and glass ampule as well as those made of plastic resin. A most preferred embodiment of the present invention consists in a prefilled syringe preparation filled in a syringe container. A prefilled syringe preparation is prepared by filling an aqueous injection solution preliminarily in a syringe container and can be stored/transported in this state as such, wherein the syringe container may or may not be provided with an injection needle. When it has no injection needle, an injection needle is fitted thereto usually upon the injection therewith. It may be considered to administer the preparation via penetration through skin by applying a high pressure to the aqueous preparation itself in the syringe, without using injection needle. Here, the outlet for the injection of the aqueous preparation at the front end may favorably be configured into a narrow orifice. For a means for increasing the internal pressure, there may be employed, for example, a pressing force by a compressed gas (nitrogen, helium, carbon dioxide etc.) and by a spring.

In selecting the buffer component(s) revealing a buffering action in the pH range mentioned above, such a buffer component(s) and an amount thereof may preferably be selected that the pH value of the charged preparation will not be altered beyond an extent of +0.3 before and after the container assigned for being filled is filled with the buffer component(s) to be examined and the so-filled container is subjected to a heating treatment at 50° C. for 96 hours, as prescribed in Examination Method 1 described afterwards, though the condition may be influenced by the kind of the buffer component, its concentration and the each specific vessel to be filled. For typical buffer components as exemplified above, the concentration therefor to be employed may be in the range of, in general, at least 0.01 mM, preferably at least 1 mM, up to, in general, at the highest 1,000 mM, preferably at the highest 200 mM, especially preferably at the highest 25 mM or at the highest 20 mM. It is preferable that the glass container is preliminarily subjected to a sulfur treatment. The glass syringe may be treated by silicone coating over its inner surface.

In an embodiment of preparation of the buffer solution based on phosphate for the aqueous injection preparation according to the present invention, an aqueous solution of sodium dihydrogenphosphate ($NaH_2PO_4$ or its 12 hydrate) of a predetermined concentration and an aqueous solution of disodium hydrogenphosphate ($Na_2HPO_4$ or its dihydrate) of also a predetermined concentration were mixed together each in a definite amount to adjust the pH at the contemplated value. Alternatively, it is also possible to add an aqueous solution of sodium hydroxide dropwise to an aqueous solution of sodium dihydrogenphosphate of a definite concentration to adjust the pH of the resulting solution at the contemplated value. It is also possible to add diluted hydrochloric acid or diluted phosphoric acid dropwise to effect a minute adjustment of the pH value. In the case of a carboxylic acid salt buffer solution typically represented by an acetate buffer, an aqueous solution of acetic acid of a predetermined concentration and an aqueous solution of sodium acetate of also a predetermined concentration are mixed together each in a definite amount to adjust the pH at the contemplated value. Alternatively, it is also possible to add an aqueous solution of sodium hydroxide of a definite concentration dropwise to an aqueous solution of acetic acid of a definite concentration to adjust the pH at the contemplated value. It is also possible to employ dropwise addition of diluted acetic acid to effect a minute adjustment of the pH value.

The aqueous injection preparation according to the present invention has usually a pH value in the range from 5.0 to 7.0, preferably from 5.5 to 6.5. Especially preferably, it has a pH of about 6.0. A preferable pH range resides in, for example, 5.5–6.0.

When the concentration of a phosphate buffer solution was, varied within a wide range from 0.2 to 200 mM, a large influence was observed on a reduction in the activity of the aqueous thrombomodulin preparation at a pH of 7.3, wherein the higher the concentration of the buffer solution was, the greater was the reduction in the activity detected. For example, the residual activity of the preparation is reduced more greater at a concentration of 200 mM. For the phosphate buffer solution, however, a favorable quality with respect to the heat stability (the long term stability) of the aqueous thrombomodulin preparation can be attained when a rigorous control of pH value within the range of 5–7.0 is effected. It is preferable to adjust a pH at 5.5–6.5, in particular at about 6.0. When an adjustment of pH at a value as close to 7.0 as possible was realized, an influence on the heat stability of the aqueous thrombomodulin preparation may be caused even by a minute fluctuation in pH value and, hence, such a pH adjustment should preferably be avoided.

In an acetate buffer solution, no influence of the concentration of the buffer solution on the quality of the thrombomodulin preparation is found even when the concentration of the buffer solution is varied within a wide range from 0.2 to 200 mM. In a buffer solution of a combination of phosphate and acetate, favorable quality with respect to the heat stability is attained in a pH range from 5.0 to 7.0.

In a buffer solution of carboxylic acid salt other than acetate, a heat stability comparable to that of acetate buffer solution is realized in the same concentration range and in the same pH range as those of the acetate buffer solution. When an acetate buffer component and/or a carboxylic acid salt buffer component is added to a phosphate buffer solution, a comparable heat stability is attained.

As the surfactant to be incorporated according to the present invention, non-ionic surfactant is preferred, for example, polysorbates, such as polysorbate 80 (of the trade name "Tween 80") and polysorbate 20 (of the trade name "Tween 20"); polyoxyethylene hydrogenated castor oils, such as polyoxyethylene hydrogenated castor oil 60 (of the trade name "HCO-60" and of the trade name of Cremophor RH 60) and polyethylene hydrogenated castor oil 50 (of the trade names "HCO-50" and "Cremophor RH 50"), polyoxyethylene castor oils (of trade names "CO-60TX", "CO-50TX" and "Cremophor EL" etc.), ethylene oxide/propylene oxide polymers, such as polyoxyethylene(160)-polyoxypropylene(30)glycol (of the trade name "Pluronic F68" etc.) and sorbitan sesquioleate. It is possible to use at least one of the surfactants selected from the group given above with permission of use of them in combination.

As to the shaking-stability, a turbidification preventive effect can be attained by an addition of at least 0.01% by weight for the polysorbate 80 (of trade name "Tween 80") and of at least 0.1% by weight for the polyoxyethylene hydrogenated castor oil (of trade name HCO-60) and the polyoxyethylene(160)polyoxy-propylene(30)glycol (of trade name "Pluronic F68"). The polysorbate 80 (trade name "Tween 80") reveals a turbidification preventive effect only at an addition of 0.01% by weight and is especially preferred.

For the concentration of the surfactant to be employed according to the present invention, there may be exemplified usually a concentration of favorably at least 0.001% by weight, preferably at least 0.01% by weight, but not more than 1% by weight, preferably not more than 0.1% by weight.

The aqueous thrombomodulin preparation according to the present invention may contain, in addition to the constituent components given above, further additives including isotonicating agent (such as sodium chloride etc.) and preservative (such as p-oxybezoic acid esters etc.) as third components.

There is no special restriction as to the practical way of incorporation of the additive ingredients in the aqueous thrombomodulin preparation, as indicated above, and such a procedure may be employed, in which they are added directly to the aqueous solution containing the thrombomodulin or they are preliminarily dissolved in water, in the water for injection or in an adequate buffer solution and the resulting solution is added to the solution of thrombomodulin.

In a preferred embodiment of preparing the aqueous thrombomodulin preparation, for example, a syringe, ampule or vial is filled with a solution of thrombomodulin in water, in water for injection or in a suitable buffer solution at a concentration of 0.05 mg or more, preferably 0.1 mg or more, especially preferably 1 mg or more, per 1 ml. While the upper limit of the thrombomodulin content is not specifically restricted, a concentration of thrombomodulin of, for example, not more than 15 mg, preferably not more than 10 mg, especially preferably not more than 6 mg, per 1 ml may be exemplified. An amount of, for example, 0.3–10 ml of an aqueous solution containing the thrombomodulin at the concentration as above and other additive ingredients is filled in the container mentioned above aseptically by a conventional technique, whereby a pharmaceutical product of the aqueous injection preparation of thrombomodulin can be obtained. For sterilizing the container, ordinary practice, for example, dry heating, autoclaving and γ-ray sterilization, may be employed. For example, a condition of at higher than 250° C. for more than 30 minutes for dry heating, at higher than 121° C. for more than 20 minutes for autoclaving and irradiation of γ-ray at a dosage of 20–60 kGy (kilograys) may be employed. For the sterilization, dry heating is usually employed for ampule and vial made of glass and autoclaving is usually employed for the rubber stopper of vial. For sterilizing syringe, usually γ-ray sterilization is employed, though autoclaving may also be possible. The aqueous solution of thrombomodulin to be filled in the container is, in general, preferably caused to pass through a sterilizing filter of pore size of 0.22 or 0.2 micrometer. The aqueous injection preparation of thrombomodulin according to the present invention is prepared by aseptically filling a sterilized container with the aseptically filtered aqueous solution of thrombomodulin. It is also preferable that the so-obtained aqueous injection preparation of thrombomodulin is packaged by a sheet or in a carton.

The aqueous injection preparation of trombomodulin according to the present invention may preferably be present as a prefilled syringe preparation, as indicated above, though it may be stored in ampule or vial. In the case of ampule preparation, it is preferable to use an ampule which has been subjected to a sulfur treatment. A sulfur-treated ampule is obtained by contacting the ampule vessel with $SO_2$ gas or favorably by spraying an aqueous ammonium sulfate solution onto the inner wall of ampule container and subjecting the so-sprayed container to a heating treatment. Usually a method of spraying 1–10% ammonium sulfate solution with subsequent heating treatment at a temperature of 630–700 Dc may be exemplified. In general, the so-treated ampule container is subjected beforehand to a further treatment on, for example, an ampule washing machine or the like, by an ultrasonication in wet state with subsequent water wash, followed by a dry heat sterilization at a temperature of 300–350 DC for several minutes, before being filled with the injection preparation.

Now, the description is directed to the method of second embodiment form of the present invention, namely, the method, wherein the aqueous injection preparation of thrombomodulin, which is characterized in that it is prepared as an asqueous solution having a pH value in the range from 5 to 7.0 and containing a soluble thrombomodulin in an effective amount and a buffer component revealing a buffering function in a pH range between 5 and 7.0 and consists of a prefilled syringe preparation filled asceptically in a syringe vessel so as to exclude any substantial gas space therein, is stored/transported in a liquid form over a long period of time.

The definitions of the soluble thrombomodulin, the buffer component and the aqueous injection preparation of thrombomodulin are the same as described previously.

For the syringe vessel to be used according to the present invention, use of commercial injection syringe may be preferred and, in general, a syringe vessel for prefilled syringe having an inner diameter of about 8.6 mm, about 6.3 mm or about 4.6 mm may be exemplified. Though selected in accordance with the charge amount of the aqueous solution of thrombomodulin, one having an inner diameter of about 4.6 mm is at the most preferable in respect of the shaking-stability, though the syringe vessel of about 6.3 mm inner diameter permits enough application. For syringe vessel of inner diameter of about 8.6 mm, it is necessary to keep the proportion of gas space in the vessel when charged with the aqueous preparation at the most 50 volume %. Thus, the syringe vessel of inner diameter of about 8.6 mm can ensure its shaking-stability so long as the proportion of gas space therein after having been filled with the aqueous preparation is kept at the most 50 volume %.

The aqueous injection preparation of trombomodulin may not, according to the specific shape and inner size of the vessel, substantially be subjected to shaking due to the surface tension thereof. In the context of this specification, "portion subject to shaking" does meen a portion of the vessel at which the aqueous injection preparation of thrombomodulin present in the vessel can be brought into motion of substantial shaking when the vessel is shaken under a condition of an amplitude of 5 cm and a frequency of 180 turns per minute at a temperature of 25° C. "The proportion of gas space" in the vessel is a value calculated by dividing the volume difference calculated by subtracting the volume of the aqueous injection preparation of thrombomodulin present within the portion subject to shaking from the volume of the portion subject to shaking, by the volume of the portion subject to shaking of the vessel, expressed in percent value. The amount of aqueous injection preparation of thrombomodulin present in the portion subject to shaking, namely, the movable amount of the aqueous injection preparation in the vessel can be confirmed by, for example, repeating an experiment for ascertaining and measuring the amount of the aqueous preparation in the vessel, which has moved downwards in the vessel after keeping the vessel filled with the aqueous injection preparation of thrombomodulin for 5 seconds in such a state, that the vertical axis and the horizontal axes of the vessel are held fixed, after it has been shaken for two minutes under the condition given above. Hereby at the same time, it is also possible to confirm the portion subject to shaking, so that the volume thereof can be determined. In the case of a syringe of simple form, the portion subject to shaking consists, of course, of the space confined between the syringe and the stopper (and the cap) itself. In the case of the syringe of about 4.6 mm inner diameter, no substantial shaking occurs and it is unnecessary to take into account of the proportion of gas space.

Usually, the syringe vessel which is sealed by a cap is filled with the aqueous injection preparation of thrombomodulin on an ordinary manner and is then fitted with a stopper. For fitting the stopper into the syringe vessel, a technique of, for example, vacuum fitting and use of a vent tube (or a sleeve) may be employed. When the syringe vessel is sealed by vacuum fitting of stopper, the proportion of gas space can relatively easily be adjusted at a value of, for example, not higher than 15 volume %. Therefore, it is to be understood by "exclude any substantial gas space" prescribed according to the present invention as a preferred embodiment that typically the proportion of gas space is not higher than 15 volume %. It is also preferred that the proportion of gas space is not higher than 10 volume %, much more that it is not higher than 5 volume %. With a syringe vessel for a prefilled syringe adapted for subcutaneous injection or for intramuscular injection (having ordinarily a capacity of several ml, preferably not greater than 2 ml, more preferably not greater than 1 ml, especially preferably not greater than 0.5 ml) having an inner diameter of at least about 8.6 mm, a prefilled syringe preparation exhibiting a superior shaking-stability can easily be attained, so long as the proportion of gas space remains below the above-given value.

Beside the syringe vessel explained above, vials and ampules may also be employed for the vessel when taking into account of incorporation of a surfactant. Ordinary vials and ampules have relatively large inner diameter and, hence, it is relatively difficult for them to decrease and adjust the proportion of gas space. Therefore, use of vials and ampules may preferably be avoided, when the proportion of gas space should be adjusted precisely.

The aqueous injection preparation of thrombomodulin prepared as above exhibits a long term stability and, thus, it can afford to preserve at least about 80% of its original activity over a period of 12 months, preferably 18 months, at 5° C. In some cases, it may permit storage/transportation over a long period of time even exceeding two years, preferably up to three years, so long as certain other conditions are satisfied.

The aqueous injection preparation of thrombomodulin according to the present invention will not suffer from occurrence of turbidity even under a condition of shaking in an amplitude of 5 cm, at a frequency of 180 turns per minute at 25° C. for one month. Thus, the aqueous injection preparation of thrombomodulin according to the present invention exhibiting such sufficient stabilities as given above can be stored/transported in a form of liquid over a long period of time.

The condition of storage/transportation to be encountered by the aqueous injection preparation of thrombomodulin according to the present invention may include a temperature higher than that causing it to freeze but not higher than room temperature and, when exemplified concretely, from 0° C. to 20° C., preferably at around 5° C. The permissible duration therefor may cover, in general, 12 months, preferably 18 months, more preferably about two years.

The aqueous injection preparation of thrombomodulin according to the present invention provides for administration forms of subcutaneous and intramuscular injections. Thus, the fourth aspect of the present invention consists in a method for applying the prefilled syringe preparation of thrombomodulin to adminitration to the patient via subcutaneous or intramuscular injection.

As the fifth aspect of the present invention consists in a method for maintaining the concentration of a soluble thrombomodulin in blood, characterized in that an aqueous injection preparation of thrombomodulin for sustained effectiveness containing an effective amount of the soluble thrombomodulin is administered to the patient via subcutaneous or intramuscular injection at an adminitration frequency of once per 2 to 5 days.

The sixth aspect of the present invention resides in a durable aqueous injection preparation of thrombomodulin containing, as the active ingredient, a soluble thrombomodulin to be administered to the patient by subcutaneous or intramuscular injection at an adminitration frequency of once per 2 to 5 days.

Since thrombomodulin exists on the surface of vascular endothelial cells and the site of action thereof is limited to within blood vessel, it has been accepted that administration of thrombomodulin by intravenous injection may bring about a direct effect and is most preferable. For example, Japanese Patent Kokai Sho 64-6219 discloses an example of drip intravenous injection thereof.

However, it is necessary to develop a medicinal preparation and so on which have conventionally not been found and which may permit an adequate choice in accordance with the condition of patient and with the practical convenience.

In the reports and publications so far, it has not always been made clear that thrombomodulin is administered to a patient intentionally via a route other than intravenous injection. Therefore, the inventors of the present invention had made research therefor and found, for the first time, that a concentration of thrombomodulin in blood can be built up, when the soluble thrombomodulin constituted of the amino acid sequence composed of amino acid residues from the site No. 19 to the site No. 516 of sequence listing SEQ ID NO: 1 (a soluble thrombomodulin obtained by transfecting the DNA segment which codes the amino acid sequence of the sequence listing SEQ ID NO: 1 to a host cell) is administered to a patient by subcutaneous injection, and that, in particular, this thrombomodulin concentration in blood is preserved over a remarkably longer time as compared with the soluble thrombomodulin constituted of the amino acid sequence composed of the residues from the site No. 367 to the site No. 480 of the sequence listing SEQ ID NO: 1.

Therefore, a preferred sustained medicinal preparation of thrombomodulin is provided according to the present invention.

It may also be favorable that a local anesthetic is further incorporated in the durable medicinal preparation mentioned above. A further content of a preservative is also preferred.

Preferred examples of the local anesthetic agent include procaine hydrochloride and benzyl alcohol. The amount of administration of the local anesthetic agent may usually be, for example, in the range of 0.5–10%, preferably 1–5%, based on the total weight of the injection preparation.

It is permissble, if necessary, that the injection preparation contains amino acids, salts, carbohydrates, surfactants, albumin, gelatin and so on, as disclosed in Japanese Patent Kokais Sho 64-6219 A and Hei 6-321805 A and so on. Addition of preservative is also favrable, wherefore preferred examples include paraoxybenzoic acid esters, such as methyl paraoxy-benzoate, ethyl paraoxybenzoate and mixtures of paraoxybenzoic acid esters. The amount of the preservative may usually be, for example, in the range from 0.01 to 1.0%, preferably from 0.1 to 0.3%, based on the weight of the injection preparation.

For the soluble thrombomodulin to be employed in the sustained medicinal preparation according to the present invention, every soluble thrombomodulin can be incorporated without any special restriction, wherein preference is given, in particular, to a soluble thrombomodulin constituted of the amino acid sequence composed of the amino acid residues from the site No. 19 to the site No. 516 of the sequence listing SEQ ID NO: 1, a soluble thrombomodulin constituted of the amino acid sequence composed of the amino acid residues from the site No. 19 to the site No. 516 of the sequence listing SEQ ID NO: 2, a soluble thrombomodulin obtained by transfecting the DNA segment which codes the amino acid sequence of the sequence listing SEQ ID NO: 1 to a host cell and a soluble thrombomodulin obtained by transfecting the DNA segment which codes the amino acid sequence of the sequence listing SEQ ID NO: 2 to a host cell.

The sustainability of the medicinal preparation according to the present inevention may favorably be exemplified by the fact that the half life of the concentration in blood ($T_{1/2}$) is at least 16 hours and that the mean retention time (MRT) in plasma is at least 36 hours.

It is preferred that the sustainable medicinal preparation according to the present invention is provided in a form of aqueous injection preparation. While the sustained medicinal preparation according to the present invention may be distributed in a form of freeze-dried product which is to be dissolved in water upon its administration, it is most convenient to use a prefilled syringe preparation prepared by filling a syringe vessel with the aqueous injection preparation of thrombomodulin described above aseptically as a subcutaneous or intramuscular injection medicine as such.

The manner of practical procedure for incorporating the additives in preparing the durable preparation according to the present invention is not specifically restricted. Thus, for example, the additives are admixed to an aqueous solution of thrombomodulin or are preliminarily dissolved in water, in water for injection or in an adequate buffer solution and the resulting solutions are then brought together in a suitable proportion before preparing the aqueous injection preparation. For example, an aqueous solution containing 0.05–15 mg, preferably 0.1–6 mg, of the soluble thrombomodulin together with the above-mentioned additives per 1 ml of water, water for injection or an adequate buffer solution is charged in, for example, a syringe vessel, a vial or, occasionally, an ampule in an amount of, for example, 0.5–10 ml, and the thereby formulated preparation is served as such for the aqueous injection preparation of thrombomodilin or, in the case of vial and ampule, the formulated preparation may further be subjected to freeze-drying. Usually the so-obtained durable medicinal preparation may contain a soluble thrombomodulin in an amount of, for example, 0.01 to 100 mg.

The administration frequency of the aqueous injection preparation of thrombomodulin according to the present invention may be, as in conventional practice, 1 to 3 administrations per day, while it is possible to select an administration frequency of, for example, once per 2–5 days. Especially, in the case of subcutaneous or intramuscular injection, an administration frequency of, for example, once per 2–5 days is preferred due to its durability. For the dosage per one administration, while it is permissible to administer the maximum permissible dose by a drip intravenous injection, usually a dosage for one single administration of at the most 1 mg of the soluble thrombomodulin per kg of the body weight is exemplified for a one-shot administration into blood vessel. For the minimum dosage, usually an amount of at least 0.001 mg, preferably at least 0.005 mg per 1 kg of the body weight may be exemplified. The upper limit of dosage for one single subcutaneous or intramuscular injection is determined by the maximum soluble amount of the active ingredient in one injection amount of the carrier liquid. A typical dosage adapted for subcutaneous or intramuscular injection is, in general, several milliliters, preferably at the most 2 ml, more preferably at the most 1 ml, especially preferably at the most 0.5 ml. Thus, a dosage expressed by the weight of the soluble thrombomodulin for one single administration by subcutaneous or intramuscular injection may usually be, for example, 20 mg or less, wherein the minimum effective amount for one single administration may, for example, be at least 0.001 mg per 1 kg of the body weight, preferably at least 0.005 mg per 1 kg of the body weight, as indicated above.

The durable preparation of thrombomodulin according to the present invention can reveal its durability by administration not only via subcutaneous but also via intramuscular route, wherein preference is given to subcutaneous injection.

It is possible according to the present invention to remarkably extend the duration in which the concentration of thrombomodulin in blood is maintained, which results in a possible reduction of administration frequency, whereby a medicinal preparation of soluble thrombomodulin effective with smaller amount as compared with that of conventional preparation for intravenous injection is provided. Such medicinal preparation can reduce patient's pain upon the injection and may permit occasionally injection by the patient himself, contributing thus to patient's therapeutic convenience considerably.

The examination for the acute toxicity of the aqueous injection preparation of soluble thrombomodulin according to the present invention has revealed that no mortal instance was found upon an administration to groups of each five male+female SD rats by intravenous injection at a dose of 180 mg/kg as the dose weight of the thrombomodulin. Also no mortal instance was seen upon administration by subcutaneous injection at the same dose of 180 mg/kg.

BRIEF DESCRIPTION OF DRAWING

FIG. 1 shows the temporal variation of the concentration of a soluble thrombomodulin in plasma after administration of the soluble thrombomodulin to rats. In the graph, IV indicates intravenous injection and SC indicates subcutaneous injection.

FREE TEXT OF SEQUENCE LISTING TABLE

Other informations in the sequence listing SEQ ID NO: 1 refer to partial amino acid sequences of a human thrombomodulin.

Other informations in the sequence listing SEQ ID NO: 2 refer to partial amino acid sequences of a human thrombomodulin.

Other informations in the sequence listing SEQ ID NO: 3 refer to partial base sequences of a human thrombomodulin gene.

Other informations in the sequence listing SEQ ID NO: 4 refer to partial base sequences of a human thrombomodulin gene.

Other informations in the sequence listing SEQ ID NO: 5 refer to the synthetic DNA for mutation.

EXAMPLE

Below, the present invention will be described concretely by way of Examples and Comparative Examples, wherein it is to be noted that the present invention is not restricted thereto.

Reference Example 1

The soluble thrombomodulins to be used in Examples are obtained in accordance with the method of Yamamoto et al (method disclosed in Example 10 of the specification of Japanese Patent Kokai Sho 64-6219). Thus, the DNA of the sequence listing SEQ ID NO: 3 was integrated in a cell of Chinese hamster ovary (CHO), to prepare a transformed cell and, by cultivating this transformed cell, soluble thrombomodulins were produced.

Reference Example 2

Primary Purification by a Strongly Basic Anion Exchange Resin 11 liters of the culture supernatant obtained in Reference Example 1, which had been frozen at minus 20° C., were thawed and filtered through a membrane filter of 0.2 μm pore size (MILLIPACK 20, a product of the firm Millipore).

The filtered culture supernatant was loaded on a Q-Sepharose column (supplied from the firm Pharmacia, with a diameter of 90 mm and a height of 6.5 cm) which had been equilibrated with a 20 mM Tris-HCl buffer solution (pH 7.4) containing 150 mM NaCl. Then, the column was washed with 20 mM acetate buffer having 180 mM NaCl and, then, was further washed with 20 mM Tris-HCl buffer solution (pH 7.4) containing 180 mM NaCl, followed by elution with 20 mM Tris-HCl buffer solution (pH 7.4) containing 300 mM NaCl, whereupon the eluate fraction from the rise-up of the 280 nm absorbance peak up to elution of 0.5 column volume was collected as a primary purified product.

Reference Example 3

Main Purification by an Affinity Column (Thrombin Column)

400 ml of the eluate fraction obtained in Reference Example 2 were dialyzed against 20 mM Tris-HCl buffer solution (pH 7.4) containing 100 mM NaCl and 0.5 mM calcium chloride. After the dialysis, the so-dialyzed solution was loaded on a DIP-thrombin-Agarose column (06-148-1035, supplied from the firm PAESE LOREI, with a diameter of 50 mm and a height of 6 cm) equilibrated with 20 mM Tris buffer solution (pH 7.4) containing 100 mM NaCl and 0.5 mM CaCl. Elution was started with 20 mM Tris buffer solution (pH 7.4) containing 1.0 M NaCl and 0.5 mM CaCla, after washing with 20 mM Tris buffer solution (pH 7.4) containing 200 mM NaCl and 0.5 mM $CaCl_2$, wherein the eluate fraction from the rise-up of the 280 nm absorbance peak to the drop-down thereof was collected as the main purified product.

Reference Example 4

Main Purification by an Affinity Column (Antibody B)

The affinity column was prepared as follows: Thus, the anti-thrombomodulin monoclonal antibody B was obtained by purifying the culture supernatant resulting from cultivation of a hybridoma producing this antibody or by purifying the abdominal dropsy resulting from cultivation of a hybridoma in the peritoneum of a histocompatible animal, such as nude mouse, by means of an isolation and purification practice, such as salting out, ion exchange chromatography or use of protein A column. Thereafter, the so-purified anti-thrombomodulin monoclonal antibody B was dissolved in 0.1 M NaHCO, buffer solution (pH 8.3) containing 0.5 M NaCl and the solution was brought into contact with a CNBr-activated Sepharose 4B (52-1153-00-AI, a product of Pharmacia) to cause the antithrombomodulin monoclonal antibody B to couple with the Sepharose 4B to build up an anti-thrombomodulin monoclonal antibody(antibody B)-coupled Sepharose 4B, in accordance with the procedures of the manual of Pharmacia (Affinity Chromatography Principles & Methods). This anti-thrombomodulin antibody (antibody B)-coupled Sepharose 4B was filled in a column to prepare a monoclonal antibody (antibody B) column.

400 ml of the eluate fraction obtained in Reference Example 2 were loaded on the monoclonal antibody (antibody B) column (with a diameter of 50 mm and a height of 6 cm) equilibrated preliminarily with 20 mM phosphate buffer solution (pH 7.3) containing 1.0 M NaCl. Then, 20 mM phosphate buffer (pH 7.3) containing 1.0 M NaCl was caused to flow through the column, followed by washing with 100 mM acetate buffer solution (pH 5.0), whereupon elution was started using 100 mM glycine-HCl buffer solution (pH 3.0) containing 0.3 M NaCl, wherein the eluate fraction from the rise-up of the 280 nm absorbance peak to the drop-down thereof was collected as the main purified product.

Reference Example 5

High-Purity Purification with Strongly Acidic Ion Exchange Column (1) Purification of eluate from the thrombin column (SP-not adsorbed fraction)

200 ml of the eluate obtained in Reference Example 3 were diluted with 100 mM glycine-HCl buffer 6m solution (pH 3.5) and the pH of the so-diluted solution was adjusted at 3.5 using 1.0 M glycine-HCl buffer solution (pH 2.0). This diluted and pH-adjusted eluate was loaded on an SP-Sepharose column (supplied from Pharmacia, with a diameter of 26 mm and a hight of 3 cm) which was preliminarily equilibrated with 100 mM glycine-HCl buffer solution (with a specific conductivity of 31 ms/cm, pH 3.5) containing 300 mM NaCl. Washing was started using 100 mM glycine-HCl buffer solution (the same as the above) having 300 mM NaCl and the eluate fraction from the rise-up of the 280 nm absorbance peak to the drop-down thereof was collected and was neutralized at once with 500 mM phosphate buffer solution (pH 7.3) to a pH of 7.0, which was served for the high purity product.

(2) Purification of Eluate from the Monoclonal Antibody Column (SP-Not Adsorbed Fraction)

180 ml of the eluate obtained in Reference Example 4 were treated with 1.0 M glycine-HCl buffer solution (pH 2.0) to adjust its pH at 3.5 and was then loaded on an SP-Sepharose column (supplied from Pharmacia, with a diameter of 26 mm and a hight of 3 cm) which was preliminarily equilibrated with 100 mM glycine-HCl buffer solution (the same as given above) containing 300 mM NaCl. Washing was started using 100 glycine-HCl buffer solution (the same as the above) containing 300 mM NaCl and the eluate fraction from the rise-up of the 280 nm absorbance peak to the drop-down thereof was collected and was neutralized at once with 500 mM phosphate buffer solution (pH 7.3) to a pH of 7.0, which was served for the high purity product.

(3) Purification of Eluate from the Thrombin Column (SP-Adsorbed Fraction)

200 ml of the eluate obtained in Reference Example 3 were diluted with 100 mM glycine-HCl buffer solution (pH 3.5) and the pH of the so-diluted solution was adjusted at 3.5 using 1.0 M glycine-HCl buffer solution (pH 2.0). This diluted and pH-adjusted eluate was loaded on an SP-Sepharose column (supplied from Pharmacia, with a diameter of 26 mm and a hight of 3 cm) which was preliminarily equilibrated with 100 mM glycine-HCl buffer solution (pH 3.5) containing 100 mM NaCl. The column was washed using 100 mM glycine-HCl buffer solution (pH 3.5) containing 100 mM NaCl and was eluted with 100 mM glycine-HCl buffer solution (pH 3.5), wherein the eluate fraction from the rise-up of the 280 nm absorbance peak to the drop-down thereof was collected and was neutralized at once with 500 mM phosphate buffer solution (pH 7.3) to a pH of 7.0, which was served for the high purity product.

(4) Purification of Eluate from the Antibody Column (SP-Adsorbed Fraction)

180 ml of the eluate obtained in Reference Example 4 were diluted with 100 mM glycine-HCl buffer solution (pH 3.5) and the pH of the so-diluted solution was adjusted at 3.5 using 1.0 M glycine-HCl buffer solution (pH 2.0). This diluted and pH-adjusted eluate was passed to an SP-Sepharose column (supplied from Pharmacia, with a diameter of 26 mm and a hight of 3 cm) which had preliminarily been equilibrated with 100 mM glycine-HCl buffer solution (pH 3.5) containing 100 mM NaCl. This column was washed using 100 mM glycine-HCl buffer solution (pH 3.5) containing 100 mM NaCl and was eluted using 100 mM glycine-HCl buffer solution (pH 3.5) containing 300 mM NaCl, whereupon the eluate fraction from the rise-up of the 280 nm absorbance peak to the drop-down thereof was collected and was neutralized at once with 500 mM phosphate buffer solution (pH 7.3) to a pH of 7.0, which was served for the high purity product.

Reference Example 6

Concentration of the High Purity Product Using Polysulfone Hollow Fiber

The high purity product obtained in Reference Example 5 was concentrated using polysulfone hollow fiber (supplied from Asahi Chemical Industry Co., Ltd.) each having a length of 1 m and having been treated with 20 mM phosphate buffer solution (pH 7.3) containing 50 mM NaCl to cause wetting thereof, whereby corresponding numbers of concentrated liquors each in an amount of 5 ml were obtained.

Reference Example 7

Exchange of the Buffer Solution of the High Purity Product Using Gel Filtration Column Each 5 ml of the concentrated high purity product obtained in Reference Example 6 were loaded on each of Sephacryl S-300 columns (of the firm Pharmacia, with a diameter of 16 mm and a height of 90 cm) which had preliminarily been equilibrated with 20 mM phosphate buffer solution (pH 7.3) containing 50 mM NaCl. This column was treated by a development with 20 mM sodium phosphate buffer solution (pH 7.3) containing 50 mM NaCl, whereupon fractional elution was effected. Each fraction was examined for the thrombomodulin activity for accelerating the activation of protein C by thrombin in accordance with the determination method 1, whereupon the fractions exhibiting such activity were collected, whereby high purity products with exchanged buffer solution were obtained.

In Examples and Comparative Examples given below, each of the high purity thrombomodulin products which were purified in the sequence order of Reference Examples 2, 4, 5(2), 6 and 7 was used. For adjusting the concentration of the buffer solution and for using a buffer component other than sodium phosphate buffer solution, the buffer component was exchanged by dialyzing the high purity product obtained as above against each respective buffer solution. By further adding a buffer solution of an adequate concentration, the concentration of the thrombomodulin was adjusted. The adjustment of pH was effected by adding a suitable amount of diluted hydrochloric acid or solution of sodium hydroxide.

The thrombomodulin obtained was confirmed to be soluble in water for injection at least at a concentration of 6 mg/ml. It was also confirmed that the molecular weight thereof is 66,000±10,000 (non-reduced state) as determined by the procedures given below:

Determination of Molecular Weight

Using a gradient electrophoresis gel (an SDS polyacrylamide gradient gel with trade name of PAGEL, 5/20%, of the firm Atto; a gel size of 90×73×1.0 mm), an electrophoresis analysis was carried out in a non-reduced state at 25° C. at a constant current of 20 mA for 90 minutes, in which a molecular weight standard (a kit for a lower molecular weight electrophoresis: a product of Pharmacia, containing, in a single vial, phosphorylase b (molecular weight=94,000), bovine serum albumin (molecular weight=67,000), ovalbumin (molecular weight=43,000), a carbonylanhydrase (molecular weight 30,000), a trypsin inhibitor (molecular weight=20,100), α-lactalbumin (molecular weight=14,400) and sucrose was used for determining the molecular weight of the thrombomodulin. Coloring was effected using Coomassie Brilliant Blue.

Reference Example 8

A soluble thrombomodulin constituted of the amino acid sequence of the residues from the 367th site to the 480th site of the sequence listing SEQ ID NO: 1 was obtained in the following manner: Thus, a plasmid obtained in accordance with the procedures given in Example 1-(1)-(b) of Japanese Patent Kokai Hei 5-213998 A was transfected to a cell by the method described in Example 1-(2) thereof, followed by purification by the procedures given in Example 3-(3) thereof, whereupon exchange of buffer solution was effected in order to obtain a high purity product of the soluble thrombomodulin.

The so-obtained soluble thrombomodulin was confirmed to be soluble in water for injection at least at a concentration of 6 mg/ml. It was further confirmed that the molecular weight thereof was 25,000±5,000 (non-reduced state) as determined by the procedures given above.

For adjusting the concentration of the buffer solution and for using a buffer component other than sodium phosphate buffer solution, buffer component was exchanged by dialyzing the high purity product obtained as above against each respective buffer solution. By further adding a buffer solution of an adequate concentration, the concentration of the thrombomodulin was adjusted. The adjustment of pH was effected by adding an adequate amount of diluted hydrochloric acid or solution of sodium hydroxide.

Reference Example 9

A soluble thrombomodulin constituted of the amino acid sequence of the residues from the 19th site to the 516th site of the sequence listing SEQ ID NO: 2 was obtained in the following manner: Thus, the technique described in Method in Enzymology, 100, 468 (1983), Academic Press, was pursued, wherein a DNA segment having the base sequence of the sequence listing SEQ ID NO: 3 was subjected to a site-specific mutation using a synthetic DNA for mutation having the base sequence of the sequence listing SEQ ID NO: 5 into a DNA which codes the amino acid sequence of sequence listing SEQ ID NO: 2, followed by the procedures of Reference Examples 1 to 7 to obtain the above-identified soluble thrombomodulin.

The so-obtained soluble thrombomodulin was confirmed to be soluble in water for injection at least at a concentration of 6 mg/ml. It was further confirmed that the molecular weight thereof was 66,000±10,000 (non-reduced state) as determined by the procedures given above.

For adjusting the concentration of the buffer solution and for using a buffer component other than sodium phosphate buffer solution, the buffer component was exchanged by dialyzing the high purity product obtained as above against each respective buffer solution. By further adding a buffer solution of an adequate concentration, the concentration of the thrombomodulin was adjusted. The adjustment of pH was effected by adding an adequate amount of diluted hydrochloric acid or solution of sodium hydroxide.

Example 1

An aqueous solution was prepared so as to adjust the concentration of the soluble thrombomodulin of Reference Example 7 at 1 mg/ml and the concentration of the sodium phosphate buffer solution at 0.2 mM, whereto NaCl and polysorbate 80 (Tween 60) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity (with inner diameter of 12 mm) and sealing the ampule. The "proportion of gas space" in the "portion subject to shaking" for this product was about 35% by volume.

Example 2

An aqueous solution was prepared so as to adjust the concentration of the soluble thrombomodulin of Reference Example 7 at 1 mg/ml and the concentration of the sodium phosphate buffer solution at 0.2 mM, whereto NaCl and a polyoxyethylene-hydrogenated castor oil (of trade name of HCO-60) were added so that their concentrations were settled at 150 mM and 0.1%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 3

An aqueous solution was prepared so as to adjust the concentration of the soluble thrombomodulin of Reference Example 7 at 1 mg/ml and the concentration of the sodium acetate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 4

An aqueous solution was prepared so as to adjust the concentration of the soluble thrombomodulin of Reference Example 7 at 1 mg/ml and the concentration of the sodium acetate buffer solution at 20 mM, whereto NaCl and a polyoxyethylene-hydrogenated castor oil (of trade name of HCO-60) were added so that their concentrations were settled at 150 mM and 0.1%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space 35%).

Example 5

An aqueous solution was prepared so as to adjust the concentration of the soluble thrombomodulin of Reference Example 7 at 1 mg/ml and the concentration of the sodium acetate buffer solution at 200 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 6

An aqueous solution was prepared so as to adjust the concentration of the soluble thrombomodulin of Reference Example 7 at 1 mg/ml and the concentration of the sodium acetate buffer solution at 20 mM, whereto NaCl and polysorbate 80 (Tween 80) were added so that their concentrations were settled at 150 mM and 0.01%, respectively, whereupon the pH thereof was adjusted at 5.5. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 7

An aqueous solution was prepared so as to adjust the concentration of the soluble thrombomodulin of Reference Example 7 at 1 mg/ml and the concentration of the sodium acetate buffer solution at 20 mM, whereto NaCl and polysorbate 80 (Tween 80) were added so that their concentrations were settled at 150 mM and 0.01%, respectively, whereupon the pH thereof was adjusted at 5.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 8

An aqueous solution was prepared so as to adjust the concentration of the soluble thrombomodulin of Reference Example 7 at 1 mg/ml and the concentration of the sodium acetate buffer solution at 2 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 9

An aqueous solution was prepared so as to adjust the concentration of the soluble thrombomodulin of Reference Example 7 at 1 mg/ml and the concentration of the sodium acetate buffer solution at 2 mM, whereto NaCl and polysorbate 80 (Tween 80) were added so that their concentrations were settled at 150 mM and 0.01%, respectively, whereupon the pH thereof was adjusted at 5.5. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 10

An aqueous solution was prepared so as to adjust the concentration of the soluble thrombomodulin of Reference Example 7 at 1 mg/ml and the concentration of the sodium acetate buffer solution at 0.2 mM, whereto NaCl and polysorbate 80 (Tween B0) were added so that their concentrations were settled at 150 mM and 0.01%, respectively, whereupon the pH thereof was adjusted at 5.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 11

An aqueous solution was prepared so as to adjust the concentration of the soluble thrombomodulin of Reference Example 7 at 1 mg/ml and the concentration of the sodium acetate buffer solution at 0.2 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%), Example 12

An aqueous solution was prepared so as to adjust the concentration of the soluble thrombomodulin of Reference Example 7 at 1 mg/ml and the concentration of the sodium acetate buffer solution at 0.2 mM, whereto NaCl and polysorbate 80 (Tween 80) were added so that their concentrations were settled at 150 mM and 0.01%, respectively, whereupon the pH thereof was adjusted at 5.5. Ampule products of aqueous injection preparation containing the soluble thrombomodulin were prepared by filling each 2 ml of the above-obtained aqueous solution into ampules of 0.2 ml capacity and sealing the ampule (proportion of gas space=35%).

Example 13

An aqueous solution was prepared so as to adjust the concentration of the soluble thrombomodulin of Reference Example 7 at 1 mg/ml and the concentration of the sodium acetate buffer solution at 0.2 mM, whereto NaCl and polysorbate 80 (Tween 80) were added so that their concentrations were settled at 150 mM and 0.01%, respectively, whereupon the pH thereof was adjusted at 5.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 14

An aqueous solution was prepared so as to adjust the concentration of the soluble thrombomodulin of Reference Example 7 at 1 mg/ml and the concentration of the sodium phosphate buffer solution at 200 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 15

An aqueous solution was prepared so as to adjust the concentration of the soluble thrombomodulin of Reference Example 7 at 1 mg/ml and the concentration of the sodium phosphate buffer solution at 200 mM, whereto NaCl and polysorbate 80 (Tween 80) were added so that their concentrations were settled at 150 mM and 0.01%, respectively, whereupon the pH thereof was adjusted at 5.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 16

An aqueous solution was prepared so as to adjust the concentration of the soluble thrombomodulin of Reference Example 7 at 1 mg/ml and the concentration of the sodium phosphate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 17

An aqueous solution was prepared so as to adjust the concentration of the soluble thrombomodulin of Reference Example 7 at 1 mg/ml and the concentration of the sodium phosphate buffer solution at 20 mM, whereto NaCl and polysorbate 80 (Tween 80) were added so that their concentrations were settled at 150 mM and 0.01%, respectively, whereupon the pH thereof was adjusted at 5.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 18

An aqueous solution was prepared so as to adjust the concentration of the soluble thrombomodulin of Reference Example 7 at 1 mg/ml and the concentration of the sodium phosphate buffer solution at 2 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 19

An aqueous solution was prepared so as to adjust the concentration of the soluble thrombomodulin of Reference Example 7 at 1 mg/ml and the concentration of the sodium phosphate buffer solution at 2 mM, whereto NaCl and polysorbate 80 (Tween 80) were added so that their concentrations were settled at 150 mM and 0.01%, respectively, whereupon the pH thereof was adjusted at 5.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 20

An aqueous solution was prepared so as to adjust the concentration of the soluble thrombomodulin of Reference Example 7 at 1 mg/ml and the concentrations of the sodium phosphate buffer solution and of the sodium acetate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 7.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 21

An aqueous solution was prepared so as to adjust the concentration of the soluble thrombomodulin of Reference Example 7 at 1 mg/ml and the concentrations of the sodium phosphate buffer solution and of the sodium acetate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 6.5. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 22

An aqueous solution was prepared so as to adjust the concentration of the soluble thrombomodulin of Reference Example 7 at 1 mg/ml and the concentrations of the sodium phosphate buffer solution and of the sodium acetate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 23

An aqueous solution was prepared so as to adjust the concentration of the soluble thrombomodulin of Reference Example 7 at 1 mg/ml and the concentrations of the sodium phosphate buffer solution and of the sodium acetate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 5.5. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 24

An aqueous solution was prepared so as to adjust the concentration of the soluble thrombomodulin of Reference Example 7 at 1 mg/ml and the concnetrations of the sodium phosphate buffer solution and of the sodium acetate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 5.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 25

An aqueous solution was prepared so as to adjust the concentration of the soluble thrombomodulin of Reference Example 7 at 1 mg/ml and the concentration of the sodium malonate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 26

An aqueous solution was prepared so as to adjust the concentration of the soluble thrombomodulin of Reference Example 7 at 1 mg/ml and the concnetration of the sodium succinate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 27

An aqueous solution was prepared so as to adjust the concentration of the soluble thrombomodulin of Reference Example 7 at 1 mg/ml and the concentration of the sodium glutarate buffer solution at 20 mM, whereto NaCl and polysorbate 80-(Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space 35%).

Example 28

An aqueous solution was prepared so as to adjust the concentration of the soluble thrombomodulin of Reference Example 7 at 1 mg/ml and the concentration of the sodium tartarate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 29

An aqueous solution was prepared so as to adjust the concentration of the soluble thrombomodulin of Reference Example 7 at 1 mg/ml and the concentration of the sodium fumarate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 30

An aqueous solution was prepared so as to adjust the concentration of the soluble thrombomodulin of Reference Example 7 at 1 mg/ml and the concentration of the sodium malate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 31

An aqueous solution was prepared so as to adjust the concentration of the soluble thrombomodulin of Reference. Example 7 at 1 mg/ml and the concentration of the sodium propionate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 32

An aqueous solution was prepared so as to adjust the, concentration of the soluble thrombomodulin of Reference Example 7 at 1 mg/ml and the concentration of the sodium citrate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 33

An aqueous solution was prepared so as to adjust the concentration of the soluble thrombomodulin of Reference Example 7 at 1 mg/ml and the concentrations of the sodium phosphate buffer solution and of the sodium A propionate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 34

An aqueous solution was prepared so as to adjust the concentration of the soluble thrombomodulin of Reference Example 7 at 1 mg/ml and the concentrations of the sodium phosphate buffer solution and of the sodium glutarate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 35

An aqueous solution was prepared so as to adjust the concentration of the soluble thrombomodulin of Reference Example 7 at 1 mg/ml and the concentrations of the sodium phosphate buffer solution and of the sodium succinate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 36

An aqueous solution was prepared so as to adjust the concentration of the soluble thrombomodulin of Reference Example 7 at 1 mg/ml and the concentrations of the sodium phosphate buffer solution and of the sodium tartarate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule. (proportion of gas space=35%).

Example 37

An aqueous solution was prepared so as to adjust the concentration of the soluble thrombomodulin of Reference Example 7 at 1 mg/ml and the concentrations of the sodium phosphate buffer solution and of the sodium fumarate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 38

An aqueous solution was prepared so as to adjust the concentration of the soluble thrombomodulin of Reference Example 7 at 1 mg/ml and the concentrations of the sodium phosphate buffer solution and of the sodium malate buffer solution at 20 mM and 20 mM, respectively, whereto NaCl and polysorbate 80 (Tween 80) were added so that their concentrations were settled at 150 mM and 0.01%, respectively, whereupon the pH thereof was adjusted at 6.0. Ampule products of aqueous Injection preparation containing the soluble thrombomodulin were prepared by filling each 2 ml of the above-obtained aqueous solution into ampules of 2 ml capacity and sealing the ampule (proportion of gas space=35%).

Example 39

An aqueous solution was prepared so as to adjust the concentration of the soluble thrombomodulin of Reference Example 7 at 1 mg/ml and the concentration of the sodium propionate buffer solution at 2 mM, whereto NaCl and polysorbate 80 (Tween 80) were added so that their concentrations were settled at 150 mM and 0.1%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 40

An aqueous solution was prepared so as to adjust the concentration of the soluble thrombomodulin of Reference Example 7 at 1 mg/ml and the concentration of the sodium phosphate buffer solution at 2 mM, whereto NaCl and a polyoxyethylene-hydrogenated castor oil (HCO-60) were added so that their concentrations were settled at 150 mM and 1%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 41

An aqueous solution was prepared so as to adjust the concentration of the soluble thrombomodulin of Reference Example 7 at 1 mg/ml and the concentration of the sodium phosphate buffer solution at 2 mM, whereto NaCl and a polyoxyethylene-hydrogenated castor oil (HCO-60) were added so that their concentrations were settled at 150 mM and 0.1%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 42

An aqueous solution was prepared so as to adjust the concentration of the soluble thrombomodulin of Reference Example 7 at 1 mg/ml and the concentration of the sodium phosphate buffer solution at 2 mM, whereto NaCl and polyoxyethylene(160)polyoxypropylene(30)glycol (trade name: Pluronic F68) were added so that their concentrations were settled at 150 mM and 1%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space 35%).

Example 43

An aqueous solution was prepared so as to adjust the concentration of the soluble thrombomodulin of Reference Example 7 at 1 mg/ml and the concentration of the sodium phosphate buffer solution at 2 mM, whereto NaCl and polyoxyethylene(160)polyoxypropylene(30)glycol (Pluronic F68) were added so that their concentrations were settled at 150 mM and 0.1%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 44

An aqueous solution was prepared so as to adjust the concentration of the soluble thrombomodulin of Reference Example 7 at 1 mg/ml and the concnetration of the sodium phosphate buffer solution at 20 mM, whereto polysorbate 80 (Tween 80) was added so that its concentration was settled at 0.01%, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Example 45

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 5% by adjusting the degree of vacuum, in order to prepare a prefilled syringe preparation for injection containing the soluble thrombomodulin.

Example 46

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 47

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 48

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 25% by adjusting the degree of vacuum, in order to prepare a prefilled syringe preparation for injection containing the soluble thrombomodulin.

Example 49

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a standard type 1 ml syringe made by the firm Becton-Dickinson, without needle) each having an inner diameter of 8.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 5% by adjusting the degree of vacuum, in order to prepare a prefilled syringe preparation for injection containing the soluble thrombomodulin.

Example 50

An aqueous solution was prepared so as to adjust the concentration of the soluble thrombomodulin of Reference Example 7 at 1 mg/ml and the concentration of La the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a standard type 1 ml syringe made by the firm Becton-Dickinson, without needle) each having an inner diameter of 8.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 51

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a standard type 1 ml syringe made by the firm Becton-Dickinson, without needle) each having an inner diameter of 8.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 52

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a standard type 1 ml syringe made by the firm Becton-Dickinson, without needle) each having an inner diameter of 8.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 25% by adjusting the degree of vacuum, in order to prepare a prefilled syringe preparation for injection containing the soluble thrombomodulin.

Example 53

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.5 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 54

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.5 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 55

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.5 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 30% by adjusting the degree of vacuum, in order to prepare a prefilled syringe preparation for injection containing the soluble thrombomodulin.

Example 56

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.5 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 40% by adjusting the degree of vacuum, in order to prepare a prefilled syringe preparation for injection containing the soluble thrombomodulin.

Example 57

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.5 ml of the so-prepared aqueous solution was filled into glass syringe vessels (a standard type 1 ml syringe made by the firm Becton-Dickinson, without needle) each having an inner diameter of 8.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 40% by adjusting the degree of vacuum, in order to prepare a prefilled syringe preparation for injection containing the soluble thrombomodulin.

Example 58

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.5 ml of the so-prepared aqueous solution was filled into glass syringe vessels (a standard type 1 ml syringe made by the firm Becton-Dickinson, without needle) each having an inner diameter of 8.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 50% by adjusting the degree of vacuum, in order to prepare a prefilled syringe preparation for injection containing the soluble thrombomodulin.

Example 59

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.5 ml of the so-prepared aqueous solution was filled into glass syringe vessels (a 0.5 ml syringe made by the firm Becton-Dickinson, with needle) each having an inner diameter of 4.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 60

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.5 ml of the so-prepared aqueous solution was filled into glass syringe vessels (a 0.5 ml syringe made by the firm Becton-Dickinson, with needle) each having an inner diameter of 4.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 61

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.3 ml of the so-prepared aqueous solution was filled into glass syringe vessels (a 0.5 ml syringe made by the firm Becton-Dickinson, with needle) each having an inner diameter of 4.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 62

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.3 ml of the so-prepared aqueous solution was filled into glass syringe vessels (a 0.5 ml syringe made by the firm Becton-Dickinson, with needle) each having an inner diameter of 4.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 35% by adjusting the degree of vacuum, in order to prepare a prefilled syringe preparation for injection containing the soluble thrombomodulin.

Example 63

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.0. Each 0.3 ml of the so-prepared aqueous solution was filled into glass syringe vessels (a 0.5 ml syringe made by the firm Becton-Dickinson, with needle) each having an inner diameter of 4.6 mm and provided each at the front end with a rubber cap (basic elastomer: bromobutyl rubber, made by the firm West) and the vessel was sealed by vacuum-fitting a rubber stopper (basic elastomer: bromobutyl rubber, mafe by the firm West) into the syringe in such a manner that the proportion of gas space was settled at 50. % by adjusting the degree of vacuum, in order to prepare a prefilled syringe preparation for injection containing the soluble thrombomodulin.

Example 64

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 5.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 65

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 5.5. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, of the firm West) and the vessel was sealed by vacuum-fitting a rubber stopper (basic elastomer: bromobutyl rubber, of the firm West) into the syringe in such a manner that the proportion of gas space was settled at 10% by adjusting the degree of vacuum, in order to prepare a prefilled syringe preparation for injection containing the soluble thrombomodulin.

Example 66

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 6.5. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West)

and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 67

An aqueous solution was prepared so as to adjust the concentration of the soluble thrombomodulin of Reference Example 7 at 1 mg/ml and the concentration of the sodium phosphate buffer solution at 2 mM, whereto NaCl was added so that its concentration was settled at 150 mM, whereupon the pH thereof was adjusted at 7.0. Each 1 ml of the so-prepared aqueous solution was filled into glass syringe vessels (a long type 0.1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, of the firm West) into the syringe in such a manner that the proportion of gas space was settled at 10. % by adjusting the degree of vacuum, in order to prepare a prefilled syringe preparation for injection containing the soluble thrombomodulin.

Example 68

An aqueous solution was prepared so as to adjust the concentration of the soluble thrombomodulin of Reference Example 7 at 1 mg/ml and the concentration of the sodium phosphate buffer solution at 20 mM, whereto NaCl was added so that its concentration was settled at 150 mM, whereupon the pH thereof was adjusted at 6.0. Each 1 ml of theso-prepared aqueous solution was filled into glass syringe vessels (a long type 1 ml syringe c: made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 69

An aqueous solution was prepared so as to adjust the concentration of the soluble thrombomodulin of Reference Example 7 at 1 mg/ml and the concentration of the sodium phosphate buffer solution at 200 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 70

An aqueous solution was prepared so as to adjust the concentration of the soluble thrombomodulin of Reference Example 7 at 1 mg/ml and the concentration of the sodium acetate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 71

An aqueous solution was prepared so as to adjust the concentration of the soluble thrombomodulin of Reference Example 7 at 1 mg/ml and the concentration of the sodium acetate buffer solution at 20 mM, whereto NaCl was added so that its concentration was settled at 150 mM, whereupon the pH thereof was adjusted at 6.0. Each 1 ml of the so-prepared aqueous solution was allotted into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 72

An aqueous solution was prepared so as to adjust the concentration of the soluble thrombomodulin of Reference Example 7 at 1 mg/ml and the concentration of the sodium acetate buffer solution at 200 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) 1.9 and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 73

An aqueous solution was prepared so as to adjust the concentration of the soluble thrombomodulin of Reference Example 7 at 0.1 mg/ml and the concentration of the sodium phosphate buffer solution at 2 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 74

An aqueous solution was prepared so as to adjust the concentration of the soluble thrombomodulin of Reference Example 7 at 0.3 mg/ml and the concentration of the sodium phosphate buffer solution at 2 mm, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 75

An aqueous solution was prepared so as to adjust the concentration of the soluble thrombomodulin of Reference Example 7 at 3 mg/ml and the concentration of the sodium phosphate buffer solution at 6 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by In adjusting the degree of vacuum, in order to prepare a prefilled syringe preparation for injection containing the soluble thrombomodulin.

Example 76

An aqueous solution was prepared so as to adjust the concentration of the soluble thrombomodulin of Reference Example 7 at 6 mg/ml and the concentration of the sodium phosphate buffer solution at 12 mM, whereto NaCl was added so that its concentration was settled at 150 mM, whereupon the pH thereof was adjusted at 6.0. Each 1 ml of the so-prepared aqueous solution was filled into glass syringe vessels (a long type 1 ml syringe made by the firm Becton-Dickinson), without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 77

An aqueous solution was prepared so as to adjust the concentration of the soluble thrombomodulin of Reference Example 7 at 3 mg/ml and the concentration of La the sodium phosphate buffer solution at 6 mM, whereto NaCl was added so that its concentration was settled at 150 mM, whereupon the pH thereof was adjusted at 6.0. Each 0.5 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 78

An aqueous solution was prepared so as to adjust the concentration of the soluble thrombomodulin of Reference Example 7 at 6 mg/ml and the concentration of the sodium phosphate buffer solution at 12 mM, whereto NaCl was added so that its concentration was settled at 150 mM, whereupon the pH thereof was adjusted at 6.0. Each 0.5 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 79

An aqueous solution was prepared so as to adjust the concentration of the soluble thrombomodulin of Reference Example 7 at 1 mg/ml and the concentration of the sodium phosphate buffer solution at 2 mM, whereto NaCl and polysorbate 80 (Tween 80) were added so that their concentrations were settled at 150 mM and 0.01%, respectively, whereupon the pH thereof was adjusted at 6.0. Each 1 ml of the so-prepared aqueous solution was filled into glass syringe vessels (a long type 1 ml syringe made by the firm Becton-Dickinson without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 80

An aqueous solution was prepared so as to adjust the concentration of the soluble thrombomodulin of Reference Example 7 at 3 mg/ml and the concentration of the sodium phosphate buffer solution at 6 mM, whereto NaCl and polysorbate 80 (Tween 80) were added so that their concentrations were settled at 150 mM and 0.01%, respectively, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 81

An aqueous solution was prepared so as to adjust the concentration of the soluble thrombomodulin of Reference Example 7 at 6 mg/ml and the concentration of the sodium phosphate buffer solution at 12 mM, whereto NaCl and polysorbate 80 (Tween 80) were added so that their concentrations were settled at 150 mM and 0.01%, respectively, whereupon the pH thereof was adjusted at 6.0. Each 0.5 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 82

An aqueous solution was prepared so as to adjust the concentration of the soluble thrombomodulin of Reference Example 7 at 6 mg/ml and the concentration of the sodium phosphate buffer solution at 12 mM, whereto NaCl and polyoxyethylene-castor oil (Cremophor EL) were added so that their concentrations were settled at 150 mM and 0.01%, respectively, whereupon the pH thereof was adjusted at 6.0. Each 0.5 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin.

Example 83

An aqueous solution was prepared so as to adjust the concentration of the soluble thrombomodulin of Reference Example 7 at 1 mg/ml and the concentrations of the sodium phosphate buffer solution and of the sodium acetate buffer solution at 20 mM and 20 mM, respectively, whereto NaCl was added so that the concentration thereof was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 84

An aqueous solution was prepared so as to adjust the concentration of the soluble thrombomodulin of Reference Example 7 at 1 mg/ml and the concentrations of the sodium phosphate buffer solution and of the in, sodium propionate buffer solution at 20 mM and 20 mM, respectively, whereto NaCl was added so that the concentration thereof was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 85

An aqueous solution was prepared so as to adjust the concentration of the soluble thrombomodulin of Reference Example 7 at 1 mg/ml and the concentrations of the sodium phosphate buffer solution and of the sodium glutarate buffer solution at 20 mM and 20 mM, respectively, whereto NaCl was added so that the concentration thereof was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front, end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 86

An aqueous solution was prepared so as to adjust the concentration of the soluble thrombomodulin of Reference Example 7 at 1 mg/ml and the concentrations of the sodium phosphate buffer solution and of the sodium succinate buffer solution at 20 mM and 20 mm, respectively, whereto NaCl was added so that the concentration thereof was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 87

An aqueous solution was prepared so as to adjust the concentration of the soluble thrombomodulin of Reference Example 7 at 1 mg/ml and the concentrations of the sodium phosphate buffer solution and of the sodium tartarate buffer solution at 20 mM and 20 mM, respectively, whereto NaCl was added so that the concentration thereof was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 88

An aqueous solution was prepared so as to adjust the concentration of the soluble thrombomodulin of Reference Example 7 at 1 mg/ml and the concentrations of the sodium phosphate buffer solution and of the sodium fumarate buffer solution at 20 mM and 20 mM, respectively, whereto NaCl was added so that the concentration thereof was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 89

An aqueous solution was prepared so as to adjust the concentration of the soluble thrombomodulin of Reference Example 7 at 1 mg/ml and the concentrations of the sodium phosphate buffer solution and of the sodium malate buffer solution at 20 mM and 20 mM, respectively, whereto NaCl was added so that the concentration thereof was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 90

An aqueous solution was prepared so as to adjust the concentration of the soluble thrombomodulin of Reference Example 9 at 1 mg/ml and the concentration of the sodium phosphate buffer solution at 20 mM, whereto NaCl and polysorbate 80 (Tween 80) were added so that their concentrations were settled at 150 mM and 0.01%, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Example 91

An aqueous solution was prepared so as to adjust the concentration of the soluble thrombomodulin of Reference Example 9 at 1 mg/ml and the concentration of the sodium phosphate buffer solution at 2 mm, whereto NaCl was added so that the concentration thereof was settled at 150 mM, whereupon the pH thereof was adjusted at 6.0. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Example 92

An aqueous solution was prepared so as to adjust the concentration of the soluble thrombomodulin of Reference Example 8 (composed of the amino acid residues from the 367th site to the 480th site of the sequence listing SEQ ID NO: 1) at 1 mg/ml and the concentration of the sodium phosphate buffer solution at 20 mM, whereto NaCl and polysorbate 80 (Tween 80) were added so that their concentrations were settled at 150 mM and 0.01 t, respectively, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space=35 i).

Comparative Example 1

An aqueous solution was prepared so as to adjust the concentration of the soluble thrombomodulin of Reference Example 7 at 1 mg/ml and the concentration of the sodium phosphate buffer solution at 20 mM, whereto NaCl was added so that the concentration thereof was settled at 150 mM, whereupon the pH thereof was adjusted at 7.3. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Comparative Example 2

An aqueous solution was prepared so as to adjust the concentration of the soluble thrombomodulin of Reference Example 7 at 1 mg/ml and the concentration of the sodium phosphate buffer solution at 20 mM, whereto NaCl was added so that the concentration thereof was settled at 150 mM, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Comparative Example 3

An aqueous solution was prepared so as to adjust the concentration of the soluble thrombomodulin of Reference Example 7 at 1 mg/ml and the concentration of the sodium phosphate buffer solution at 0.2 mM, whereto NaCl was added so that the concentration thereof was settled at 150 mM, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Comparative Example 4

An aqueous solution was prepared so as to adjust the concentration of the soluble thrombomodulin of Reference Example 7 at 1 mg/ml and the concentration of the sodium acetate buffer solution at 20 mM, whereto NaCl was added so that the concentration thereof was settled at 150 mM, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Comparative Example 5

An aqueous solution was prepared so as to adjust the concentration of the soluble thrombomodulin of Reference Example 7 at 1 mg/ml and the concentration of the sodium phosphate buffer solution at 200 mM, whereto NaCl and polysorbate 80 (Tween 80) were added so that their concentrations were settled at 150 mM and 0.01%, respectively, whereupon the pH thereof was adjusted at 7.3. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Comparative Example 6

An aqueous solution was prepared so as to adjust the concentration of the soluble thrombomodulin of Reference Example 7 at 1 mg/ml and the concentration of mM the sodium phosphate buffer solution at 20 mM, whereto NaCl and polysorbate 80 (Tween 80) were added so that their concentrations were settled at 150 mM and 0.01%, respectively, whereupon the pH thereof was adjusted at 7.3. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Comparative Example 7

An aqueous solution was prepared so as to adjust the concentration of the soluble thrombomodulin of Reference Example 7 at 1 mg/ml and the concentration of the sodium phosphate buffer solution at 2 mM, whereto NaCl and polysorbate 80 (Tween 80) were added so that their concentrations were settled at 150 mM and 0.01%, respectively, whereupon the pH thereof was adjusted at 7.3. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Comparative Example 8

An aqueous solution was prepared so as to adjust the concentration of the soluble thrombomodulin of Reference Example 7 at 1 mg/ml and the concentrations of the sodium phosphate buffer solution and of the sodium acetate buffer solution at 20 mM and 20 mM, respectively, whereto NaCl and polysorbate 80 (Tween 80) were added so that their concentrations were settled at 50 mM and 0.01%, respectively, whereupon the pH thereof was adjusted at 7.3. Ampule products of aqueous injection preparation containing the soluble thrombomodulin were prepared by filling each 2 ml of the above-obtained aqueous solution into ampules of 2 ml capacity and sealing the ampule (proportion of gas space=35%).

Comparative Example 9

An aqueous solution was prepared so as to adjust the concentration of the soluble thrombomodulin of Reference Example 7 at 1 mg/ml and the concentration of the sodium phosphate buffer solution at 2 mM, whereto NaCl was added so that the concentration thereof was settled at 150 mM, whereupon the pH thereof was adjusted at 7.3. Ampule products of aqueous injection preparation containing the soluble thrombomodulin were prepared by filling each 2 ml of the above-obtained aqueous solution into ampules of 2 ml capacity and sealing the ampule. Here, the proportion of gas space in the portion subject to shaking was 35%.

Comparative Example 10

An aqueous solution was prepared so as to adjust the concentration of the soluble thrombomodulin of Reference Example 7 at 1 mg/ml and the concentration of the sodium phosphate buffer solution at 2 mM, whereto NaCl was added so that the concentration thereof was settled at 150 mM, whereupon the pH thereof was adjusted at 7.3. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Comparative Example 11

An aqueous solution was prepared so as to adjust the concentration of the soluble thrombomodulin of Reference Example 7 at 1 mg/ml and the concentration of the sodium phosphate buffer solution at 2 mM, whereto NaCl was added so that the concentration thereof was settled at 150 mM, whereupon the pH thereof was adjusted at 6.0. Each 0.5 ml of the so-prepared aqueous solution was filled into glass syringe vessels (a standard type 1 ml syringe made by the firm Becton-Dickinson, without needle) each having an inner diameter of 8.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 60% by adjusting the degree of vacuum, in order to prepare a prefilled syringe preparation for injection containing the soluble thrombomodulin.

Comparative Example 12

An aqueous solution was prepared so as to adjust the concentration of the soluble thrombomodulin of Reference Example 7 at 1 mg/ml and the concentration of the sodium phosphate buffer solution at 2 mM, whereto NaCl was added so that the concentration thereof was settled at 150 mM, whereupon the pH thereof was adjusted at 6.0. Each 0.5 ml of the so-prepared aqueous solution was filled into glass syringe vessels (a standard type 1 ml syringe made by the firm Becton-Dickinson, without needle) each having an inner diameter of 8.6 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 70% by adjusting the degree of vacuum, in order to prepare a prefilled syringe preparation for injection containing the soluble thrombomodulin.

Comparative Example 13

An aqueous solution was prepared so as to adjust the concentration of the soluble thrombomodulin of Reference Example 7 at 1 mg/ml and the concentration of the sodium phosphate buffer solution and 20 mM, whereto NaCl was added so that the concentration thereof was settled at 150 mM, whereupon the pH thereof was adjusted at 7.3. Each 1 ml of the so-prepared aqueous solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin.

Comparative Example 14

An aqueous solution was prepared so as to adjust the concentration of the soluble thrombomodulin of Reference Example 9 at 1 mg/ml and the concentration of the sodium phosphate buffer solution at 20 mM, whereto NaCl was added so that th concentration thereof was settled at 150 mM, whereupon the pH thereof was adjusted at 6.0. Ampule products of aqueous injection preparation containing the soluble thrombomodulin were prepared by filling each 2 ml of the above-obtained aqueous solution into ampules of 2 ml capacity and sealing the ampule (proportion of gas space= 35%).

Comparative Example 15

An aqueous solution was prepared so as to adjust the concentration of the soluble thrombomodulin of Reference Example 8 at 1 mg/ml and the concentration of the sodium phosphate buffer solution at 20 mM, whereto NaCl was added so that the concentration thereof was settled at 150 mM, whereupon the pH thereof was adjusted at 6.0. Ampule products of aqueous injection in preparation containing the soluble thrombomodulin were prepared by filling each 2 ml of the above-obtained aqueous solution into ampules of 2 ml capacity and sealing the ampule (proportion of gas space= 35%).

Test Example 1

The rate of preservation of the activity (namely, percent residual activity) was determined for each of the aqueous injection preparations of thrombomodulin of Examples 1 to 4 and of Comparative Examples 1 to 4 for estimating the stabilities against heat of them in accordance with the procedures of Examination Method 1 given below. The preparations which have residual activity values of at least 66% determined by Examination Method 1 after having been held at 50° C. for 96 hours are judged as "passed". According to the prediction from Arrhenius' plotting, the preparations having residual activity of at least 66% are assumed to have a life, in which the preparation has a residual activity of at least 80% when preserved at 5° C., of three years. On the other hand, an evaluation of the stability against shaking was performed in accordance with the procedures of Examination Method 2 given below. The preparation which was judged to be satisfactory by both Examination Methods 1 and 2 is integrally evaluated as "proper", while others are put down as "improper". The results are summarized in Table 1.

TABLE 1

|  | Comparative Example | | | | Example | | | |
| --- | --- | --- | --- | --- | --- | --- | --- | --- |
|  | 1 | 2 | 3 | 4 | 1 | 2 | 3 | 4 |
| Buffer solution | Na—PO$_4$ [1] | Na—PO$_4$ | Na—PO$_4$ | Na—Ac [2] | Na—PO$_4$ | Na—PO$_4$ | Na—Ac | Na—Ac |
| (concentration) | (20 mM) | (20 mM) | (0.2 mM) | (20 mM) | (0.2 mM) | (0.2 mM) | (20 mM) | (20 mM) |
| stored at pH of | 7.3 | 6.0 | 6.0 | 6.0 | 6.0 | 6.0 | 6.0 | 6.0 |

TABLE 1-continued

|  | Comparative Example | | | | Example | | | |
| --- | --- | --- | --- | --- | --- | --- | --- | --- |
|  | 1 | 2 | 3 | 4 | 1 | 2 | 3 | 4 |
| Surfactant (concentration) | none | none | none | none | Tween 80 (0.01%) | HCO-60 (0.1%) | Tween 80 (0.01%) | HCO-60 (0.1%) |
| Examin. Method 1 % resid. activity | 55.4 | 79.1 | 83.4 | 86.7 | 84.7 | 85.4 | 87.8 | 84.4 |
| Examin. Method 2 |  |  |  |  |  |  |  |  |
| Appearance | turbid | turbid | turbid | turbid | clear [3] | clear | clear | clear |
| Turbidity | — | — | 2.930 | 2.930 | 0.000 | 0.002 | 0.002 | 0.002 |
| % resid. activity | — | — | 98.4 | 99.6 | 100.6 | 101.0 | 101.8 | 102.5 |
| Evaluation | improper | improper | improper | improper | proper | proper | proper | proper |

Notes:
[1] Na—PO$_4$ = sodium phosphate buffer
[2] Na—Ac = sodium acetate buffer
[3] clear = colorless and transparent As shown in Table 1, all the preparations with both sodium phosphate buffer solution and sodium acetate buffer solution had percent residual activitys higher than 66% at pH 6.0 in the test for stability against heat, whereas the preparation of Comparative Example 1 of pH 7.3 had a value lower than 66%. When a surfactant, namely, Tween 80 or HCO-60, was present, an aqueous injection preparation which did not become turbid on the shaking-stability test and was evaluated integrally as "proper" was obtained.

(Examination Method 1)

Test for Stability against Heat (While Heating at 50° C. for 96 Hours)

The aqueous injection preparation to be tested was subjected to a heat treatment at 50° C. for 96 hours, whereupon the activity of the thrombomodulin thereof was determined, in order to assess the activity preservation rate (percent residual activity) by comparing the observed activity value of the heat treated injection preparation with the original value of the preparation stored under freezing without subjecting to heat treatment which is assumed to be 100%.

The determination of the activity of thrombomodulin of an aqueous preparation is performed by observing the function of the preparation for accelerating the activation of protein C by thrombin (APC assay). Thus, 5 µl of a sample solution, which was prepared suitable from an aqueous injection preparation containing a soluble thrombomodulin so that the thrombomodulin was contained therein, by an adequate dilution, in an amount in the range from 0.35 to 1.4 ng, are added to 37.5 µl of a 50 mM Tris-HCl buffer solution (pH=8.5) containing 100 mM NaCl, 3 mM calcium chloride, 0.1% bovine serum albumin (supplied from the firm Sigma) and 0.225 NIHU of human thrombin (supplied from the firm Sigma) and the mixture is stood still for 15 minutes at 37° C., whereto 7.5 µl of bovine protein C of about 300 µg/ml (supplied from the firm Life Technologies) are added and the resulting mixture is again stood still for 30 minutes at 37° C. in order to activate the protein C. Then, about 7.5 µl of an aqueous solution containing about 100 µl/ml of a heparin (supplied from Wako Pure Chemical Ind., Ltd.) and about 6 µl/ml of Antithrombin III (of the firm Life Technologies) are added to the mixture to terminate the reaction. To this mixture are then added 500 µl of a solution containing 1° C. p g/ml of a synthetic substrate (Boc-Leu-Ser-Thr-Arg-MCA) (SEQ ID NO: 6) and the resulting mixture is stood still for 20 minutes at 37° C. The substrate-scissoring reaction is then terminated by adding 50 µl of acetic acid. The reaction mixture is examined by observing the fluorescence strength at an excitation wave length of 380 nm and at an emission wave length of 440 nm using a fluorescence spectrophotometer to determine the amount of the existing activated protein C, whereupon the thrombomodulin activity is calculated by comparison with a reference preparation of standard thrombomodulin activity.

(Examination Method 2)

Test for Stability Against Shaking (Under Shaking at 180 Reciprocations per Minute)

An aqueous injection preparation to be tested is subjected to a shaking treatment in a constant temperature shaker at 25° C. under a condition of an amplitude of 5 cm and a reciprocation of 180 turns per minute for one month, in order to observe change in the appearance before and after the shaking treatment. If necessary, turbidity (absorbance at 650 nm) and the residual activity of thrombomodulin are determined. The direction of the reciprocation movement is settled to be parallel to the longitudinal axis of the testing vessel. The practical procedures for the determination of thrombomodulin activity are the same as in Examination Method 1.

Test Example 2

Tests were carried out by Examination Methods 1 and 2 for the aqueous injection preparations of Examples 3, 5 to 13 and of Comparative Example 1, to thereby assess overall evaluations, for them in a similar way. The results are summarized in Table 2.

TABLE 2

|  | Compar. Example | Example | | | | | | | | | | |
| --- | --- | --- | --- | --- | --- | --- | --- | --- | --- | --- | --- | --- |
|  | 1 | 3 | 5 | 6 | 7 | 8 | 9 | 10 | 11 | 12 | 13 |
| Buffer solution (concentration) | Na—PO$_4$ [1] (20 mM) | Na—Ac [2] (20 mM) | Na—Ac (20 mM) | Na—Ac (20 mM) | Na—Ac (20 mM) | Na—Ac (2 mM) | Na—Ac (2 mM) | Na—Ac (2 mM) | Na—Ac (0.2 mM) | Na—Ac (0.2 mM) | Na—Ac (0.2 mM) |
| stored at pH of | 7.3 | 6.0 | 6.0 | 5.5 | 5.0 | 6.0 | 5.5 | 5.0 | 6.0 | 5.5 | 5.0 |

TABLE 2-continued

|  | Compar. Example | Example | | | | | | | | | | |
| --- | --- | --- | --- | --- | --- | --- | --- | --- | --- | --- | --- | --- |
|  | 1 | 3 | 5 | 6 | 7 | 8 | 9 | 10 | 11 | 12 | 13 |
| Surfactant (concentration) | none | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) |
| Examin. Method 1 % resid. activity | 55.4 | 87.8 | 85.4 | 90.3 | 75.1 | 85.4 | 79.0 | 75.7 | 84.4 | 80.9 | 77.4 |
| Examin. Method 2 |  |  |  |  |  |  |  |  |  |  |  |
| Appearance | turbid | clear [3] | clear | clear | clear | clear | clear | clear | clear | clear | clear |
| Turbidity | — | — | — | — | — | — | — | — | — | — | — |
| % resid. activity | — | — | — | — | — | — | — | — | — | — | — |
| Evaluation | improper | proper | proper | proper | proper | proper | proper | proper | proper | proper | proper |

Notes:
[1] Na—PO$_4$ = sodium phosphate buffer
[2] Na—Ac = sodium acetate buffer
[3] clear = colorless and transparent As shown in Table 2, there was no influence due to alteration of the buffer solution concentration on varying the concentration of sodium acetate buffer solution within the range from 0.2 to 200 mM and all the aqueous preparations had residual activities higher than 66% in the heat stability test. In the presence of 0.01% of Tween 80, no occurrence of turbidity was recognized in the shaking-stability test and aqueous injection preparations exhibiting the overall evaluation "proper" were obtained.

Test Example 3

Tests were carried out by Examination Methods 1 and 2 for the aqueous injection preparations of Examples 14 to 19 and of Comparative Examples 5 to 7, to thereby assess overall evaluations for them in a similar way. The results are summarized in Table 3.

As shown in Table 3, an influence due to alteration of the buffer solution concentration was recognized at pH 7.3 on varying the concentration of sodium phosphate buffer solution within a wide range from 2 to 200 mM but all the aqueous preparations had residual activities higher than 66% in the heat stability test, so long as the pH of the preparation was in the range of 5.0–6.0. In the presence of 0.01% of Tween 80, no occurrence of turbidity was recognized in the shaking-stability test and aqueous injection preparations exhibiting the overall evaluation "proper" were obtained.

Test Example 4

Tests were carried out by Examination Methods 1 and 2 for the aqueous injection preparations of Examples 20 to 24 and of Comparative Examples 1 and 8, to thereby assess overall evaluations for them in a similar way. The results are summarized in Table 4.

TABLE 3

|  | Compar. Example | Example | | Compar. Example | Example | | Compar. Example | Example | |
| --- | --- | --- | --- | --- | --- | --- | --- | --- | --- |
|  | 5 | 14 | 15 | 6 | 16 | 17 | 7 | 18 | 19 |
| Buffer solution (concentration) | Na—PO$_4$ [1] (200 mM) | Na—PO$_4$ (200 mM) | Na—PO$_4$ (200 mM) | Na—PO$_4$ (20 mM) | Na—PO$_4$ (20 mM) | Na—PO$_4$ (20 mM) | Na—PO$_4$ (2 mM) | Na—PO$_4$ (2 mM) | Na—PO$_4$ (2 mM) |
| stored at pH of | 7.3 | 6.0 | 5.0 | 7.3 | 6.0 | 5.0 | 7.3 | 6.0 | 5.0 |
| Surfactant (concentration) | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) |
| Examin. Method 1 % residual titer | 7.1 | 73.7 | 67.8 | 54.1 | 88.2 | 72.3 | 63.2 | 86.8 | 70.3 |
| Examin. Method 2 |  |  |  |  |  |  |  |  |  |
| Appearance | clear [3] | clear | clear | clear | clear | clear | clear | clear | clear |
| Turbidity | — | — | — | — | — | — | — | — | — |
| % resid. activity | — | — | — | — | — | — | — | — | — |
| Evaluation | improper | proper | proper | improper | proper | proper | improper | proper | proper |

Notes:
[1] Na—PO$_4$ = sodium phosphate buffer
[3] clear = colorless and transparent

TABLE 4

|  | Compar. Example | | Example | | | | |
| --- | --- | --- | --- | --- | --- | --- | --- |
|  | 1 | 8 | 20 | 21 | 22 | 23 | 24 |
| Buffer solution (concentration) | Na—PO$_4$ [1] (20 mM) | Na—PO$_4$ (20 mM), Na—Ac [2] (20 mM) | Na—PO$_4$ (20 mM), Na—Ac (20 mM) | Na—PO$_4$ (20 mM), Na—Ac (20 mM) | Na—PO$_4$ (20 mM), Na—Ac (20 mM) | Na—PO$_4$ (20 mM), Na—Ac (20 mM) | Na—PO$_4$ (20 mM), Na—Ac (20 mM) |
| stored at pH of | 7.3 | 7.3 | 7.0 | 6.5 | 6.0 | 5.5 | 5.0 |
| Surfactant (concentration) | none | Tween 80 (0.01%) | Tween 80 (0.01%) | Tween 80 (0.01%) | Tween 80 (0.01%) | Tween 80 (0.01%) | Tween 80 (0.01%) |
| Examin. Method 1 % resid. activity | 55.4 | 59.8 | 68.9 | 74.2 | 81.3 | 80.7 | 71.3 |
| Examin. Method 2 |  |  |  |  |  |  |  |
| Appearance | turbid | clear [3] | clear | clear | clear | clear | clear |
| Turbidity | — | — | — | — | — | — | — |
| % resid. activity | — | — | — | — | — | — | — |
| Evaluation | improper | improper | proper | proper | proper | proper | proper |

Notes:
[1] Na—PO$_4$ = sodium phosphate buffer
[2] Na—Ac = sodium acetate buffer
[3] clear = colorless and transparent As shown in Table 4, all the aqueous injection preparations, of which pH values were in the range of 5.0–7.0, had residual activities higher than 66% in the heat stability test, when the concentrations of buffer components, i.e. sodium phosphate buffer solution and sodium acetate buffer solution, were both adjusted at 20 mM and the pH of the aqueous preparation was varied in the range from 5.0 to 7.3. Within the pH range of 5.5–6.5, the aqueous preparations had residual activities higher than 73% in the heat stability test, which is assumed to correspond to a life of the preparation for being stored at 5° C., while preserving at least 80% of the original activity. In particular, the residual activities for the preparations having pH values of 5.5 and 6.0 were as high as more than 80%. On the other hand, the residual activity was lower than 66% at pH 7.3 (Reference Examples 1 and 8). In the presence of 0.01% of Tween 80, no occurrence of turbidity was recognized in the shaking-stability test and aqueous injection preparations exhibiting the overall evaluation "proper" were obtained.

Test Example 5

Tests were carried out by Examination Methods 1 and 2 for the aqueous injection preparations of Examples 25 to 32 and of Comparative Examples 1 and 2, to thereby assess overall evaluations for them in a similar way. The results are summarized in Table 5.

TABLE 5

|  | Compar. Example | | Example | | | | | | | |
| --- | --- | --- | --- | --- | --- | --- | --- | --- | --- | --- |
|  | 1 | 2 | 25 | 26 | 27 | 28 | 29 | 30 | 31 | 32 |
| Buffer solution (concentration) | Na—PO$_4$ [1] (20 mM) | Na—PO$_4$ (20 mM) | Sodium malonate (20 mM) | Sodium succinate (20 mM) | Sodium glutarate (20 mM) | Sodium tartarate (20 mM) | Sodium fumarate (20 mM) | Sodium malate (20 mM) | Sodium propionate (20 mM) | Sodium citrate (20 mM) |
| stored at pH of | 7.3 | 6.0 | 6.0 | 6.0 | 6.0 | 6.0 | 6.0 | 6.0 | 6.0 | 6.0 |
| Surfactant (concentration) | none | none | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) | Tween 80 (0.01%) |
| Examin. Method 1 % resid. activity | 55.4 | 79.1 | 85.9 | 81.7 | 82.4 | 74.5 | 77.3 | 77.0 | 79.2 | 74.5 |
| Examin. Method 2 |  |  |  |  |  |  |  |  |  |  |
| Appearance | turbid | turbid | clear [3] | clear | clear | clear | clear | clear | clear | clear |
| Turbidity | — | — | — | — | — | — | — | — | — | — |
| % resid. activity | — | — | — | — | — | — | — | — | — | — |
| Evaluation | improper | improper | proper | proper | proper | proper | proper | proper | proper | proper |

Notes:
[1] Na—PO$_4$ = sodium phosphate buffer
[3] clear = colorless and transparent As shown in Table 5, all the residual activities were higher than 66% when the pH was settled at 6.0, even if the buffer solution was changed to that of 20 mM of varying carboxylic acid salt. In the presence of 0.01% of Tween 80, no occurrence of turbidity was recognized in the shaking-stability test and aqueous injection preparations exhibiting the overall evaluation "proper" were obtained.

Test Example 6

Tests were carried out by Examination Methods 1 and 2 for the aqueous injection preparations of Examples 33 to 38 and of Comparative Examples 1 and 2, to thereby assess overall evaluations for them in a similar way. The results are summarized in Table 6.

TABLE 6

|  | Compar. Example | | Example | | | | | |
| --- | --- | --- | --- | --- | --- | --- | --- | --- |
|  | 1 | 2 | 33 | 34 | 35 | 36 | 37 | 38 |
| Buffer solution (concentration) | Na—PO$_4$ [1] (20 mM) | Na—PO$_4$ (20 mM) | Na—PO$_4$ (20 mM), Sodium propionate (20 nM) | Na—PO$_4$ (20 mM), Sodium glutarate (20 mM) | Na—PO$_4$ (20 mM), Sodium succinate (20 mM) | Na—PO$_4$ (20 mM), Sodium tartarate (20 mM) | Na—PO$_4$ (20 mM), Sodium fumarate (20 mM) | Na—PO$_4$ (20 mM), Sodium malate (20 mM) |
| stored at pH of | 7.3 | 6.0 | 6.0 | 6.0 | 6.0 | 6.0 | 6.0 | 6.0 |
| Surfactant (concentration) | none | none | Tween 80 (0.01%) | Tween 80 (0.01%) | Tween 80 (0.01%) | Tween 80 (0.01%) | Tween 80 (0.01%) | Tween 80 (0.01%) |
| Examin. Method 1 % resid. activity | 55.4 | 79.1 | 78.0 | 76.1 | 82.1 | 81.3 | 72.6 | 84.3 |
| Examin. Method 2 |  |  |  |  |  |  |  |  |
| Appearance | turbid | turbid | clear [3] | clear | clear | clear | clear | clear |
| Turbidity | — | — | — | — | — | — | — | — |
| % resid. activity | — | — | — | — | — | — | — | — |
| Evaluation | improper | improper | proper | proper | proper | proper | proper | proper |

Notes:
[1] Na—PO$_4$ = sodium phosphate buffer
[3] clear = colorless and transparent As shown in Table 6, all the residual activities were higher that 66% when the pH was settled at 6.0, even if buffer component of varying carboxylic acid salt was added to the sodium phosphate buffer solution. In the presence 01% of Tween 80, no occurrence of turbidity was recognized in the shaking-stability test and aqueous injection preparations exhibiting the overall evaluation "proper" were obtained.

Test Example 7

Tests were carried out by Examination Methods 1 and 2 for the aqueous injection preparations of Examples 18, 39, 43 and 44 and of Comparative Example 9, to thereby assess overall evaluations for them in a similar way. The results are summarized in Table 7.

As shown In Table 7, the aqueous preparation without surfactant (Comparative Example 9) became turbid on testing the shaking-stability by shaking the testing sample with varying surfactant at varying concentration, whereas, in the samples with surfactant, occurrence of turbidity was prevented. Enough effect was attained at a concentration of 0.1%, for the surfactant with the trade name of Tween 80, and 0.1%, for the surfactants with the trade names of HCO-60 and of Pluronic F68. No influence of sodium chloride was recognized.

Test Example 8

Tests were carried out by Examination Methods 1 and 2 for the aqueous injection preparations of Examples 45 to 63 and of Comparative Examples 10 to 12, to thereby assess overall evaluations for them in a similar way. The results are summarized in Table 8.

TABLE 7

|  | Compar. Example | Example | | | | | | |
| --- | --- | --- | --- | --- | --- | --- | --- | --- |
|  | 9 | 39 | 18 | 40 | 41 | 42 | 43 | 44 |
| Buffer solution (concentration) | Na—PO$_4$ [1] (2 mM) | Na—PO$_4$ (2 mM) | Na—PO$_4$ (2 mM) | Na—PO$_4$ (2 mM) | Na—PO$_4$ (2 mM) | Na—PO$_4$ (2 mM) | Na—PO$_4$ (2 mM) | Na—PO$_4$ (20 mM) |
| stored at pH of | 7.3 | 6.0 | 6.0 | 6.0 | 6.0 | 6.0 | 6.0 | 6.0 |
| Surfactant (concentration) | none | Tween 80 (0.1%) | Tween 80 (0.01%) | HCO-60 (1%) | HCO-60 (0.1%) | Pluronic F68 (1%) | Pluronic F68 (0.1%) | Tween 80 (0.01%) |
| Examin. Method 1 % resid. activity | improper | passed | passed | passed | passed | passed | passed | passed |
| Examin. Method 2 |  |  |  |  |  |  |  |  |
| Appearance | turbid | clear [3] | clear | clear | clear | clear | clear | clear |
| Turbidity | 1.299 | −0.008 | −0.010 | 0.017 | −0.003 | 0.010 | −0.004 | — |
| % resid. activity | 90.8 | 97.6 | 87.0 | 87.8 | 93.8 | 101.7 | 93.2 | — |
| Evaluation | improper | proper | proper | proper | proper | proper | proper | proper |

Notes:
[1] Na—PO$_4$ = sodium phosphate buffer
[3] clear = colorless and transparent

TABLE 8

| | Comparative Example | | | Example | | | | | | | |
|---|---|---|---|---|---|---|---|---|---|---|---|
| | 10 | 11 | 12 | 45 | 46 | 47 | 48 | 49 | 50 | 51 | 52 |
| Buffer solution (concentration) stored at pH of | Na—PO$_4$ [1] (2 mM) 7.3 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 |
| Porportion of gas space (%) | 10 | 60 | 70 | 5 | 10 | 15 | 25 | 5 | 10 | 15 | 25 |
| Examin. Method 1 % resid. activity | improper | passed | passed | passed | 86.5 | passed | passed | passed | passed | passed | 93.2 |
| Examin. Method 2 | | | | | | | | | | | |
| Appearance | clear [3] | turbid | turbid | clear | clear | clear | clear | clear | clear | clear | clear |
| Turbidity | 0.012 | 0.124 | 0.182 | 0.004 | 0.006 | 0.019 | 0.010 | 0.005 | 0.008 | 0.010 | 0.049 |
| % resid. activity | — | 92.9 | 95.3 | 97.8 | 98.6 | 96.8 | 93.2 | 93.2 | 92.7 | 90.7 | 92.7 |
| Evaluation | improper | improper | improper | proper | proper | proper | proper | proper | proper | proper | proper |

| | Example | | | | | | | | | | |
|---|---|---|---|---|---|---|---|---|---|---|---|
| | 53 | 54 | 55 | 56 | 57 | 58 | 59 | 60 | 61 | 62 | 63 |
| Buffer solution (concentration) stored at pH of | Na—PO$_4$ [1] (2 mM) 6.0 | Na—PO$_4$ (2 mM) 6.0 | Na—PO$_4$ (2 nM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 | Na—PO$_4$ (2 mM) 6.0 |
| Porportion of gas space (%) | 10 | 15 | 30 | 40 | 40 | 50 | 10 | 15 | 15 | 35 | 50 |
| Examin. Method 1 % resid. activity | passed | passed | passed | 80.9 | passed | passed | passed | passed | passed | passed | passed |
| Examin. Method 2 | | | | | | | | | | | |
| Appearance | clear [3] | clear | clear | clear | clear | clear | clear | clear | clear | clear | clear |
| Turbidity | 0.005 | 0.018 | 0.013 | 0.018 | 0.016 | 0.045 | 0.020 | 0.005 | 0.022 | 0.015 | 0.014 |
| % resid. activity | 96.5 | 95.8 | 96.8 | 97.8 | 97.2 | 92.8 | — | — | — | — | — |
| Evaluation | proper | proper | proper | proper | proper | proper | proper | proper | proper | proper | proper |

Notes:
[1] Na—PO$_4$ = sodium phosphate buffer
[3] clear = colorless and transparent As shown in Table 8, no occurrence of turbidity was recognized in the shaking-stability test when the proportion of gas space in the portion subject to shaking was lower than 50 volume %, whereas, in the samples of Reference Examples 11 and 12 in which the proportion of gas space is 60 volume % and 70 volume %, respectively, occurrence of turbidity was observed upon shaking. In the case of adjusting the pH value at 6.0, the residual activity in the heat stability test was higher than 66% and aqueous injection preparations exhibiting the overall evaluation "proper" were obtained.

Test Example 9

Tests were carried out by Examination Methods 1 and 2 for the aqueous injection preparations of Examples 46 and 64 to 72 and of Comparative Example 10, to thereby assess overall evaluations for them in a similar way. The results are summarized in Table 9.

TABLE 9

| | Compar. Example | Example | | | | | | | | | |
|---|---|---|---|---|---|---|---|---|---|---|---|
| | 10 | 46 | 64 | 65 | 66 | 67 | 68 | 69 | 70 | 71 | 72 |
| Buffer solution (concentration) stored at pH of | Na—PO$_4$ [1] (2 mM) 7.3 | Na—PO$_4$ (2 mM) 6.0 | Na—PO$_4$ (2 mM) 5.0 | Na—PO$_4$ (2 mM) 5.5 | Na—PO$_4$ (2 mM) 6.5 | Na—PO$_4$ (2 mM) 7.0 | Na—PO$_4$ (20 mM) 6.0 | Na—PO$_4$ (200 mM) 6.0 | Na—Ac [2] (2 mM) 6.0 | Na—Ac (20 mM) 6.0 | Na—Ac (200 mM) 6.0 |
| Porportion of gas space (%) | 10 | 10 | 10 | 10 | 10 | 10 | 10 | 10 | 10 | 10 | 10 |
| Examin. Method 1 % resid. activity | improper | 86.5 | 66.2 | 75.9 | 75.9 | 67.2 | 79.6 | 74.6 | 92.4 | 88.4 | 91.8 |

TABLE 9-continued

|  | Compar. Example | Example | | | | | | | | | |
| --- | --- | --- | --- | --- | --- | --- | --- | --- | --- | --- | --- |
|  | 10 | 46 | 64 | 65 | 66 | 67 | 68 | 69 | 70 | 71 | 72 |
| Examin. Method 2 | | | | | | | | | | | |
| Appearance | clear [3] | clear | clear | clear | clear | clear | clear | clear | clear | clear | clear |
| Turbidity | 0.012 | 0.006 | 0.020 | 0.022 | 0.013 | 0.013 | 0.007 | 0.016 | 0.014 | 0.015 | 0.016 |
| % resid. activity | — | 98.6 | 87.9 | 94.8 | 90.9 | 93.0 | — | — | — | — | — |
| Evaluation | improper | proper | proper | proper | proper | proper | proper | proper | proper | proper | proper |

Notes:
[1] Na—PO$_4$ = sodium phosphate buffer
[2] Na—Ac = sodium acetate buffer
[3] clear = colorless and transparent As shown in Table 9, there was no influence by the alteration of concentration of sodium phosphate buffer solution or sodium acetate buffer solution within a wide range of 2–200 mM and all the residual activities were higher than 66% in the heat stability test when the pH was adjusted within the range of 5.0–7.0. In case the proportion of gas space was settled at 10%, no occurence of turbidity was observed in the shaking-stability test and aqueous injection preparations exhibiting the overall evaluation "proper" were obtained.

Test Example 10

Tests were carried out by Examination Methods 1 and 2 for the aqueous injection preparations of Examples 46, 73 to 82 and 90 to 92 and of Comparative Examples 13 to 15, to thereby assess overall evaluations for them in a similar way. The results are summarized in Table 10.

TABLE 10

|  | Compar. Example | Example | | | | | | | | | |
| --- | --- | --- | --- | --- | --- | --- | --- | --- | --- | --- | --- |
|  | 13 | 73 | 74 | 46 | 75 | 76 | 77 | 78 | 79 | 80 | 81 |
| Buffer solution (concentration) | Na—PO$_4$ [1] (20 mM) | Na—PO$_4$ (2 mM) | Na—PO$_4$ (2 mM) | Na—PO$_4$ (2 mM) | Na—PO$_4$ (6 mM) | Na—PO$_4$ (12 mM) | Na—PO$_4$ (6 mM) | Na—PO$_4$ (12 mM) | Na—PO$_4$ (2 mM) | Na—PO$_4$ (6 mM) | Na—PO$_4$ (12 mM) |
| stored at pH of | 7.3 | 6.0 | 6.0 | 6.0 | 6.0 | 6.0 | 6.0 | 6.0 | 6.0 | 6.0 | 6.0 |
| Surfactant (concentration) | none | none | none | none | none | none | none | none | Tween 80 (0.01%) | Tween 80 (0.01%) | Tween 80 (0.01%) |
| Examin. Method 1 % resid. activity | 51.9 | 89.1 | 84.4 | 86.5 | passed | passed | 69.9 | 82.2 | passed | passed | passed |
| Examin. Method 2 | | | | | | | | | | | |
| Appearance | clear [3] | clear | clear | clear | clear | clear | clear | clear | clear | clear | clear |
| Turbidity | 0.004 | 0.009 | 0.014 | 0.006 | 0.015 | 0.019 | 0.042 | 0.028 | 0.004 | 0.002 | 0.002 |
| % resid. activity | 87.9 | 94.5 | 97.8 | 98.6 | 89.8 | 95.2 | 99.4 | 101.9 | 95.6 | 96.7 | 96.9 |
| Evaluation | improper | proper | proper | proper | proper | proper | proper | proper | proper | proper | proper |

|  | Example | | | | Compar. Example |
| --- | --- | --- | --- | --- | --- |
|  | 82 | 90 | 91 | 92 | 14 |
| Buffer solution (concentration) | Na—PO$_4$ [1] (12 mM) | Na—PO$_4$ (20 mM) | Na—PO$_4$ (2 mM) | Na—PO$_4$ (20 mM) | Na—PO$_4$ (20 mM) |
| stored at pH of | 6.0 | 6.0 | 6.0 | 6.0 | 6.0 |
| Surfactant (concentration) | Cremophor EL (0.01%) | Tween 80 (0.01%) | none | Tween 80 (0.01%) | none |
| Examin. Method 1 % resid. activity | passed | passed | passed | passed | passed |

TABLE 10-continued

|  | Examin. Method 2 | | | | |
|---|---|---|---|---|---|
| Appearance | clear [3] | clear | clear | clear | turbid |
| Turbidity | 0.000 | — | — | — | — |
| % resid. activity | 94.8 | — | — | — | — |
| Evaluation | proper | proper | proper | proper | improper |

Notes:
[1] Na—PO$_4$ = sodium phosphate buffer
[3] clear = colorless and transparent As shown in Table 10, no influence of change in the concentration of thrombomodulin was recognized at least in the range from 0.1 mg/ml to 6 mg/ml and all the residual activities were higher than 66% when adjusting the pH value at 6.0. When the proportion of gas space was settled at 10–15%, no occurrence of turbidity was recognized in the shaking-stability test and aqueous injection preparations exhibiting the overall evaluation "proper" were obtained.

According to Comparative Example 14, it was confirmed that there is a problem of shaking-stability also in the soluble thrombomodulin of Reference Example 9. By the results of Examples 90 and 91, it was confirmed that an aqueous injection preparation of soluble thrombomodulin superior in the heat stability and in the shaking-stability was also obtained according to the present Invention using the soluble thrombomodulin of Reference Example 9.

In Example 92 in which the soluble thrombomodulin of Reference Example 8 was used, an aqueous injection preparation superior in the heat stability and in the shaking-stability was obtained.

Test Example 11

Tests were carried out by Examination Method 3 for accelerated stability given below for the aqueous injection preparations of Examples 1, 3 and 79 to 82 and of Comparative Examples 6 and 13, wherein residual activity was determined after storage at 20° C. The results are summarized in Table 11.

As shown in Table 11, the aqueous injection preparations of Examples 1, 3 and 79 to 82 were discernibly stable, whereas those of Comparative Examples 6 and 13 showed decreases of residual activity down to 52.4% and to 63.2%, respectively, after storage at 20° C. for 6 months.

(Examination Method 3)

Accelerated Stability Test (Stored at 20° C. for 6 months)

The aqueous injection preparation to be tested is stored at 20° C. for 6 months, whereupon the residual activity of thrombomodulin is determined. The determination of thrombomodulin tactivity is carried out in the same manner as Examination Method 1.

Test Example 12

Tests were carried out by Examination Method 4 for long term stability given below for the aqueous injection preparations of Examples 1 and 3, wherein residual activity of thrombomodulin was determined after storage at 5° C. The determination of thrombomodulin activity is carried out in the same manner as Examination Method 1. The results are summarized in Table 12.

TABLE 11

|  | Compar. Example | | Example | | | | | |
|---|---|---|---|---|---|---|---|---|
|  | 6 | 13 | 1 | 3 | 79 | 80 | 81 | 82 |
| Buffer solution | Na—PO$_4$ [1] | Na—PO$_4$ | Na—PO$_4$ | Na—Ac [2] | Na—PO$_4$ | Na—PO$_4$ | Na—PO$_4$ | Na—PO$_4$ |
| (concentration) | (20 mM) | (20 mM) | (0.2 mM) | (20 mM) | (2 mM) | (6 mM) | (12 mM) | (12 mM) |
| stored at pH of | 7.3 | 7.3 | 6.0 | 6.0 | 6.0 | 6.0 | 6.0 | 6.0 |
| Surfactant | Tween 80 | none | Tween 80 | Tween 80 | Tween 80 | Tween 80 | Tween 80 | Cremophor EL |
| (concentration) | (0.01%) |  | (0.01%) | (0.01%) | (0.01%) | (0.01%) | (0.01%) | (0.01%) |
| Examin. Method 3 Resid. activity % after |  |  |  |  |  |  |  |  |
| 0 month | 100 | 100 | 100 | 100 | 100 | 100 | 100 | 100 |
| 3 months | 67.1 | 81.8 | 92.5 | 97.5 | 92.8 | 94.4 | 93.4 | 94.0 |
| 6 months | 52.4 | 63.2 | 73.7 | 80.1 | 65.4 | 85.6 | 84.9 | 82.5 |

Notes:
[1] Na—PO$_4$ = sodium phosphate buffer
[2] Na—Ac = sodium acetate buffer

TABLE 12

|  | Example | |
|---|---|---|
|  | 1 | 3 |
| Buffer solution (concentration) | Na—PO$_4$ [1] (0.2 mM) | Na—Ac [2] (20 mM) |
| stored at pH of | 6.0 | 6.0 |
| Surfactant (concentration) | Tween 80 (0.01%) | Tween 80 (0.01%) |
| Examin. Method 3 Resid. activity % after |  |  |
| 0 month | 100 | 100 |
| 3 months | 97.3 | 105.3 |
| 6 months | 93.1 | 101.5 |
| 9 months | 97.9 | 107.6 |

Notes:
[1] Na—PO$_4$ = sodium phosphate buffer
[2] Na—Ac = sodium acetate buffer The aqueous preparations of Examples 1 and 3 did not show any decrease in the thrombomodulin activity after storage at 5° C. for 9 months.
(Examination Method 4)
Long Term Stability Test (Stored at 5° C. for 9 Months)
The aqueous injection preparation to be tested is stored at 5° C. for 9 months, whereupon the residual activity of thrombomodulin is determined. The determination of thrombomodulin activity is carried out in the same manner as in Examination Method 1.

Test Example 13

A test solution or test preparation given below was administered to male SD rats of 9–10 week ages via tail vein or subcutaneous route at dorsum and blood-collection was effected at adequate interval.
1) Test solutions for intravenous Injection
Test solutions for intravenous injection were prepared by adjusting the concentrations of the soluble thrombomodulin of Reference Example 7 in the high purity product thereof at 10 M g/ml, 50 μg/ml and 250 μg/ml, respectively, and the concentration of the sodium phosphate buffer solution at 10 mM and adding thereto NaCl at a concentration of 150 mM and polysorbate 80 (Tween 80) at a concentration of 0.01%, whereupon the pH was adjusted at 7.4. These test solutions were administered each at a dose as given in Table 13.
2) Test solutions A for Subcutaneous Injection
Test solutions were prepared by adjusting the concentrations of the soluble thrombomodulin of Refernce Example 7 in the high purity product thereof at 10 μg/ml, 50 μg/ml and 250 μg/ml, respectively, and the concentration of the sodium phosphate buffer solution at 10 mM and adding thereto NaCl at a concentration of 150 mM, polysorbate 80 (Tween 80) at a concentration of 0.01%, pharmacopeial benzyl alcohol at a concentration of 40 mg/ml and methyl p-oxybenzoate at a concentration of 0.3%, whereupon the pH was adjusted at 7.4 to obtain test solutions A. These test solutions were administered each at a dose as given in Table 13.
3) Test Solutions B for Subcutaneous Injection
Test solutions were prepared by adjusting the concentrations of the soluble thrombomodulin of Refernce Example 7 in the high purity product thereof at 10 μg/ml, 50 μg/ml and 250 μg/ml, respectively, and the concentration of the sodium phosphate buffer solution at 10 mM and adding thereto NaCl at a concentration of 150 mM, polysorbate 80 (Tween 80) at a concentration of 0.01%, pharmacopeial procaine hydrochloride at a concentration of 40 mg/ml and methyl p-oxybenzoate at a concentration of 0.3%, whereupon the pH was adjusted at 7.4 to obtain test solutions B.
4) Test Preparation C for Subcutaneous Injection
A test solution was prepared by adjusting the concentration of the soluble thrombomodulin of Refernce Example 7 in the high purity product thereof at 250 μg/ml and the concentration of the sodium phosphate buffer solution at 2 mM and adding thereto NaCl at a concentration of 150 mM, whereupon the pH was adjusted at 6.0. Each 1 ml of this solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 10% by adjusting the degree of vacuum, in order to prepare a prefilled syringe preparation for injection containing the soluble thrombomodulin. By fitting to this prefilled preparation for injection a plunger rod (a plunger for 1 ml long type syringe made of polypropylene, supplied from the firm Becton-Dickinson) and an injection needle (26 G×½", supplied from the firm Terumo), a ready-to-use test preparation C for subcutaneous injection was obtained.
5) Test Preparation D for Subcutaneous Injection
A test solution was prepared by adjusting the concentration of the soluble thrombomodulin of Refernce Example 7 in the high purity product thereof at 250 μg/ml and the concentration of the sodium phosphate buffer solution at 2 mM and adding thereto NaCl at a concentration of 150 mM and polysorbate 80 (Tween 80) at a concentration of 0.01%, whereupon the pH was adjusted at 6.0. Each 0.5 ml of this solution was filled into glass syringe vessels (a long type 1 ml syringe made by the firm Becton-Dickinson, without needle) each having an inner diameter of 6.3 mm and provided each at the front end with a rubber cap (basic elastomer: bromobutyl rubber, made by the firm West) and the vessel was sealed by vacuum-fitting a rubber stopper (basic elastomer: bromobutyl rubber, made by the firm West) into the syringe in such a manner that the proportion of gas space was settled at 15% by adjusting the degree of vacuum, in order to prepare a prefilled syringe preparation for injection containing the soluble thrombomodulin. By fitting to this prefilled syringe preparation for injection a plunger rod (a plunger for 1 ml long type syringe made of polypropylene, supplied from the firm Becton-Dickinson) and an injection needle (26 G×½", supplied from the firm Terumo), a ready-to-use test preparation D for subcutaneous injection was obtained.

TABLE 13

| Route of administration | Solution tested | Conc. (μg/ml) | Dose amount (ml/kg) | Dosage (μg/kg) | Times injected |
|---|---|---|---|---|---|
| Intravenous | Test solition for i. v. injection | 10 | 1 | 10 | thrice |
| Intravenous | Test solition for i. v. injection | 50 | 1 | 50 | thrice |
| Intravenous | Test solition for i. v. injection | 250 | 1 | 250 | thrice |
| Subcutaneous | Test solution A for s. c. injection | 10 | 1 | 10 | thrice |
| Subcutaneous | Test solution A for s. c. injection | 50 | 1 | 50 | thrice |
| Subcutaneous | Test solution A for s. c. injection | 250 | 1 | 250 | thrice |

The concentration of the soluble thrombomodulin in the blood was pursued after the administration by determining it by enzyme-linked immunosorbent assay (ELISA) at each point of time, the results of which are shown in FIG. 1. For the practical procedures of the determining of thrombomodulin, a known technique of an ELISA, in which R4B6 as the antibody of stationary phase and R4D1 as the labelling antibody were coupled, was employed (Japanese Patent Kokai Hei 6-205692 A). Some parameters pharmacokinetics based on the course of variation of the values of the concentration of thrombomodulin in blood are given in Table 14.

TABLE 14

| Route of administration | Solution tested | Dosage (μg/kg) | $T_{max}$ (hr) | $C_{max}$ (ng/ml) | $T_{1/2}$ (hr) | AUC (0–∞) (μg · hr/ml) | MRT (hr) |
|---|---|---|---|---|---|---|---|
| Intravenous | Test solition for i. v. injection | 10 | 0 | 322.7 | 6.1 | 2.02 | 6.1 |
| Intravenous | Test solition for i. v. injection | 50 | 0 | 1346.2 | 7.8 | 10.75 | 7.9 |
| Intravenous | Test solition for i. v. injection | 250 | 0 | 6138.3 | 7.2 | 44.79 | 7.2 |
| Subcutaneous | Test solution A for s. c. injection | 10 | 32.2 | 21.4 | 17.4 | 1.06 | 38.4 |
| Subcutaneous | Test solution A for s. c. injection | 50 | 23.4 | 140.3 | 19.9 | 7.01 | 38.8 |
| Subcutaneous | Test solution A for s. c. injection | 250 | 8.3 | 661.5 | 16.7 | 42.67 | 36.6 |

As shown in Table 14, it was found that the mean residence time (MRT) is greater for administration via subcutaneous route than for administration via intravenous route in all dosages. In addition it was also confirmed, as seen in FIG. 1, that the durable time for maintaining the concentration in blood is markedly longer for the subcutaneous administration than for the intravenous administration. It was confirmed that $T_{1/2}$ values can be extended as long as 16 hours or more by subcutaneous administration.

In the groups administered with the subcutaneous injection test solution B and with the subcutaneous preparations C and D, nearly the same results were obtained as the subcutaneous injection teat solution A. From these facts, it was confirmed that better function of maintaining more effective level of the concentration of thrombomodulin in blood for therapy is attained by subcutaneous administration than administration via intravenous route as in conventional practice. The biological availability value (BA) upon subcutaneous administration was found to be higher than 50% for all the dosages, indicating a better absoptibility.

When the pH values of the test solutions for subcutaneous administration were varied in the range of 3.0–7.4, no special difference was recognized in the concentration in blood. By altering the Ion intensity of the test solution to be administered (variation of NaCl strength in the range from 0 to 4.8%), no special change was recognized in the concentration of the effective agent in blood.

What is claimed is:

1. A method for storing/transporting an aqueous injection preparation of thrombomodulin in a non-frozen or non-freeze dried liquid form, comprising:

preparing an aqueous solution having a pH value in a range from 5 to 7.0, wherein said solution contains soluble thrombomodulin and contains buffer component(s) having a buffering action in a pH range between 5 and 7.0, wherein said aqueous solution further comprises a surfactant, aseptically packing said aqueous solution in a container wherein said aqueous solution is kept aseptically in the container while being stored/transported, packaging said container filled with the aqueous solution for storage/transportation in a sheet or in a carton, and storing and/or transporting said aqueous injection-preparation of thrombomodulin in a non-frozen or non-freeze dried liquid form.

2. The method according to claim 1 wherein the soluble thrombomodulin is selected from the group consisting of thrombomodulin comprising the sequence of amino acids 19 to 516 of SEQ ID NO:1, thrombomodulin comprising the sequence of amino acids 19 to 516 of SEQ ID NO: 2, that obtained by transfecting a DNA segment coding an amino acid sequence given in the sequence listing SEQ ID NO: 1 to a host cell and that obtained by transfecting DNA segment coding an amino acid sequence given in the sequence listing SEQ ID NO: 2 to a host cell.

3. The method according to claim 1, wherein the pH of the buffer solution is in the range from 5.5 to 6.5.

4. The method according to claim 1, wherein said aqueous solution contains 0.05 to 15 mg/ml of soluble thrombomodulin.

5. A method for storing/transporting an aqueous injection preparation of thrombomodulin in a non-frozen or non-freeze dried liquid form, comprising:

preparing an aqueous solution having a pH value in a range from 5 to 7.0, wherein said solution contains soluble thrombomodulin and contains buffer component(s) having a buffering action in a pH range between 5 and 7.0, wherein said aqueous solution further comprises a surfactant, aseptically packing said aqueous solution in a container wherein said aqueous solution is kept aseptically in the container while being stored/transported and said container filled with the aqueous solution is a prefilled syringe preparation, wherein the aqueous solution is in a syringe vessel sealed aseptically by a cap and a stopper, packaging said container filled with the aqueous solution for storage/transportation in a sheet or in a carton, and storing and/or transporting said aqueous injection preparation of thrombomodulin in a non-frozen or non-freeze dried liquid form.

6. The method according to claim 5, wherein said prefilled syringe preparation is for subcutaneous injection or for intramuscular injection.

7. The method according to claim 5, wherein the said prefilled syringe preparation is characterized in that the aqueous solution of thrombomodulin occupies the syringe container in an amount so that residual gas space therein does not exceed 15% by volume in terms of the proportion of gas space.

8. The method according to claim 5, wherein the prefilled syringe preparation is characterized in that the aqueous solution of thrombomodulin occupies the syringe container in such an amount that residual gas space therein does not exceed 10% by volume in terms of the proportion of gas space.

9. The method according to claim 5, wherein the prefilled syringe preparation is characterized in that the aqueous solution of thrombomodulin occupies the syringe container in such an amount that residual gas space therein does not exceed 5% by volume in terms of the proportion of gas space.

10. The method according to claim 5, wherein the inner diameter of the syringe container is 8.6 mm or less.

* * * * *